US009260502B2

(12) United States Patent
Nielsen et al.

(10) Patent No.: US 9,260,502 B2
(45) Date of Patent: Feb. 16, 2016

(54) PROTEASE-STABILIZED INSULIN ANALOGUES

(75) Inventors: Peter Kresten Nielsen, Holte (DK); Frantisek Hubalek, Herlev (DK); Inger Lautrup-Larsen, Virum (DK); Per Balschmidt, Hørsholm (DK); Svend Ludvigsen, Lynge (DK); Thomas Børglum Kjeldsen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 898 days.

(21) Appl. No.: 12/922,106

(22) PCT Filed: Mar. 13, 2009

(86) PCT No.: PCT/EP2009/053019
§ 371 (c)(1),
(2), (4) Date: Dec. 10, 2010

(87) PCT Pub. No.: WO2009/112583
PCT Pub. Date: Sep. 17, 2009

(65) Prior Publication Data
US 2011/0092419 A1 Apr. 21, 2011

Related U.S. Application Data

(60) Provisional application No. 61/037,429, filed on Mar. 18, 2008.

(30) Foreign Application Priority Data

Mar. 14, 2008 (EP) ..................................... 08102598

(51) Int. Cl.
A61K 38/16 (2006.01)
C07K 14/00 (2006.01)
C07K 14/62 (2006.01)
A61K 38/00 (2006.01)

(52) U.S. Cl.
CPC *C07K 14/62* (2013.01); *A61K 38/00* (2013.01)

(58) Field of Classification Search
None
See application file for complete search history.

(56) References Cited

U.S. PATENT DOCUMENTS

| | | |
|---|---|---|
| 2,832,685 A | 4/1958 | Everette |
| 3,528,960 A | 9/1970 | Haas |
| 3,719,655 A | 3/1973 | Jackson et al. |
| 3,869,437 A | 3/1975 | Lindsay et al. |
| 3,950,517 A | 4/1976 | Lindsay et al. |
| 4,033,941 A | 7/1977 | Stilz et al. |
| 4,179,337 A | 12/1979 | Davis et al. |
| 5,149,777 A | 9/1992 | Hansen et al. |
| 5,179,189 A | 1/1993 | Domb et al. |
| 5,359,030 A | 10/1994 | Ekwuribe |
| 5,446,020 A | 8/1995 | Andy et al. |
| 5,478,575 A | 12/1995 | Miyazaki et al. |
| 5,506,202 A | 4/1996 | Vertesy et al. |
| 5,506,203 A | 4/1996 | Backstrom et al. |
| 5,597,796 A | 1/1997 | Brange |
| 5,716,927 A | 2/1998 | Balschmidt et al. |
| 5,898,067 A | 4/1999 | Balschmidt et al. |
| 5,922,675 A | 7/1999 | Baker et al. |
| 6,221,837 B1 | 4/2001 | Ertl et al. |
| 6,251,856 B1 | 6/2001 | Markussen et al. |
| 6,475,795 B1 | 11/2002 | Turley et al. |
| 6,500,645 B1 | 12/2002 | Kjeldsen et al. |
| 6,746,853 B1 * | 6/2004 | Dahiyat et al. ............... 435/69.1 |
| 6,770,625 B2 | 8/2004 | Soltero et al. |
| 6,867,183 B2 | 3/2005 | Soltero et al. |
| 6,869,930 B1 | 3/2005 | Havelund et al. |
| 7,030,082 B2 | 4/2006 | Soltero et al. |
| 7,030,083 B2 | 4/2006 | Schreiner et al. |
| 2002/0045731 A1 | 4/2002 | Schaffer et al. |
| 2002/0198140 A1 | 12/2002 | Havelund |
| 2003/0027748 A1 | 2/2003 | Ekwuribe et al. |
| 2003/0035775 A1 | 2/2003 | Klibanov |
| 2003/0083232 A1 | 5/2003 | Soltero et al. |
| 2003/0104981 A1 | 6/2003 | Mandic |
| 2003/0134294 A1 | 7/2003 | Sandford et al. |
| 2003/0166508 A1 | 9/2003 | Zhang |
| 2004/0038867 A1 | 2/2004 | Still et al. |
| 2004/0097410 A1 | 5/2004 | Zheng et al. |
| 2004/0198949 A1 | 10/2004 | Ekwuribe et al. |
| 2004/0254119 A1 | 12/2004 | West et al. |
| 2005/0276843 A1 | 12/2005 | Quay et al. |
| 2006/0019874 A1 | 1/2006 | Radhakrishnan et al. |
| 2006/0183668 A1 | 8/2006 | Jonassen et al. |
| 2007/0096431 A1 | 5/2007 | Mochizuki et al. |
| 2008/0076705 A1 | 3/2008 | Kodra et al. |

(Continued)

FOREIGN PATENT DOCUMENTS

| | | |
|---|---|---|
| CN | 1390854 A | 1/2003 |
| EP | 265213 A2 | 4/1988 |

(Continued)

OTHER PUBLICATIONS

Bajaj, 1986, Biochem J., 238, 345-351.*
Website:http://cancerweb.ncl.ac.uk/omd/about.html, 5 pages, Jul. 7, 2005.*
Bajaj et al., "Coypu Insulin: Primary Structure, Conformation and Biological Properties of a Hystricomorph Rodent Insulin", Journal of Biochemistry, 1986, Vol. 238, pp. 345-351.
Bennett, R.G., et al, "Insulin inhibition of the proteasome is dependent on degradation of insulin by insulin-degrading enzyme" Journal of Endocrinology, 2003, vol. 177, pp. 399-405.
Brange et al. ("Design of Novel Insulins with Changed Self-Association and Ligand Binding Properties," GBF Monographs, 1989, 12, 139-144).

(Continued)

*Primary Examiner* — Satyanarayana R Gudibande
(74) *Attorney, Agent, or Firm* — Jianjie Hu

(57) ABSTRACT

The present invention relates to novel insulin analogs comprising mutations at position A14 in the A chain and at positions B27, B28, B29 and B30 in the B chain and exhibiting resistance towards protease; a method for the preparation of such insulin analogs; insulin preparations containing the insulin analogs of the invention; and, a method of treating diabetes mellitus using these insulin analogs.

4 Claims, No Drawings

(56) References Cited

U.S. PATENT DOCUMENTS

| | | |
|---|---|---|
| 2008/0171695 A1 | 7/2008 | Garibay et al. |
| 2011/0105720 A1 | 5/2011 | Madsen et al. |

FOREIGN PATENT DOCUMENTS

| | | | |
|---|---|---|---|
| EP | 376156 A2 | 7/1990 | |
| EP | 511600 A2 | 11/1992 | |
| EP | 712861 A2 | 5/1996 | |
| EP | 712862 A2 | 5/1996 | |
| EP | 837072 A2 | 4/1998 | |
| EP | 925792 A2 | 6/1999 | |
| EP | 1121144 A1 | 4/2000 | |
| EP | 1002547 A1 | 5/2000 | |
| EP | 0894095 | 5/2003 | |
| GB | 1492997 A | 11/1977 | |
| JP | 57-067548 A | 4/1982 | |
| JP | 1254699 A | 10/1989 | |
| JP | H03504240 A | 9/1991 | |
| JP | H03-506023 A | 12/1991 | |
| JP | H09502867 A | 3/1997 | |
| JP | H10509176 | 8/1998 | |
| JP | 11-502110 | 2/1999 | |
| JP | 2000-501419 A | 2/2000 | |
| JP | 2000-504732 A | 4/2000 | |
| JP | 2001-521004 A | 11/2001 | |
| JP | 2001-521006 A | 11/2001 | |
| JP | 2001-521904 A | 11/2001 | |
| JP | 2002-308899 A | 10/2002 | |
| JP | 2002-543092 A | 12/2002 | |
| JP | 2003-518917 A | 6/2003 | |
| RU | 2146139 C1 | 3/2000 | |
| WO | 8910937 A1 | 11/1989 | |
| WO | 90/01038 A1 | 2/1990 | |
| WO | 90/12814 A1 | 11/1990 | |
| WO | 91/12817 A1 | 9/1991 | |
| WO | 92/00321 A1 | 1/1992 | |
| WO | 92/00322 A1 | 1/1992 | |
| WO | 92/01476 A1 | 2/1992 | |
| WO | 92/12999 A1 | 8/1992 | |
| WO | 94/08599 A1 | 4/1994 | |
| WO | 95/07931 A1 | 3/1995 | |
| WO | 95/13795 A1 | 5/1995 | |
| WO | 95/24183 A1 | 9/1995 | |
| WO | 96/15803 A1 | 5/1996 | |
| WO | WO 96/29344 | 9/1996 | |
| WO | 96/37215 A1 | 11/1996 | |
| WO | 97/31022 A1 | 8/1997 | |
| WO | 98/01473 A1 | 1/1998 | |
| WO | 98/02460 A1 | 1/1998 | |
| WO | 99/21888 A1 | 5/1999 | |
| WO | 99/24071 A1 | 5/1999 | |
| WO | 99/65941 A1 | 12/1999 | |
| WO | 00/00176 A1 | 1/2000 | |
| WO | 00/10541 A1 | 3/2000 | |
| WO | 00/23098 A1 | 4/2000 | |
| WO | 00/43034 A2 | 7/2000 | |
| WO | 0042993 | 7/2000 | |
| WO | 00/61178 A1 | 10/2000 | |
| WO | 00/69901 A2 | 11/2000 | |
| WO | 00/78302 A1 | 12/2000 | |
| WO | 02/094200 A2 | 11/2002 | |
| WO | 02098232 | 12/2002 | |
| WO | 02098446 A1 | 12/2002 | |
| WO | 03/013573 | 2/2003 | |
| WO | 03/022208 A2 | 3/2003 | |
| WO | 03/022996 A2 | 3/2003 | |
| WO | 03/047493 A2 | 6/2003 | |
| WO | 03/048195 A2 | 6/2003 | |
| WO | 03/053339 A2 | 7/2003 | |
| WO | 03/094951 A1 | 11/2003 | |
| WO | 03/094956 A1 | 11/2003 | |
| WO | 2004/105790 A1 | 12/2004 | |
| WO | 2005/005477 A2 | 1/2005 | |
| WO | 2005/012346 A1 | 2/2005 | |
| WO | 2005/012347 A2 | 2/2005 | |
| WO | 2005/016312 A1 | 2/2005 | |
| WO | 2005/047508 A1 | 5/2005 | |
| WO | 2005/049061 A2 | 6/2005 | |
| WO | 2005/055976 A2 | 6/2005 | |
| WO | 2005/058961 A2 | 6/2005 | |
| WO | 2005/092301 A1 | 10/2005 | |
| WO | 2006/023943 A1 | 3/2006 | |
| WO | 2006060753 A2 | 6/2006 | |
| WO | 2006/079641 A2 | 8/2006 | |
| WO | 2006/082204 A1 | 8/2006 | |
| WO | 2006/082205 A1 | 8/2006 | |
| WO | 2006/097521 A1 | 9/2006 | |
| WO | 2007/006320 A1 | 1/2007 | |
| WO | 2007/041481 A1 | 4/2007 | |
| WO | 2007/047948 A2 | 4/2007 | |
| WO | 2007/074133 A2 | 7/2007 | |
| WO | 2007/081824 A2 | 7/2007 | |
| WO | WO 2007/096332 | 8/2007 | |
| WO | WO 2007/096431 | 8/2007 | |
| WO | 2007/104737 A1 | 9/2007 | |
| WO | 2007/128815 A1 | 11/2007 | |
| WO | 2007/128817 A2 | 11/2007 | |
| WO | 2008/015099 A2 | 2/2008 | |
| WO | WO 2008/015099 | * 2/2008 | |
| WO | 2008/034881 A1 | 3/2008 | |
| WO | WO 2008/132229 | 11/2008 | |
| WO | WO 2008/145730 | 12/2008 | |
| WO | WO 2009/010428 | 1/2009 | |
| WO | 2009/022005 A1 | 2/2009 | |
| WO | 2009/022006 A1 | 2/2009 | |
| WO | 2009/112583 A2 | 9/2009 | |
| WO | 2009/115469 A1 | 9/2009 | |

OTHER PUBLICATIONS

Yip, C.C. et al. "Structure and function of Insulin: Preparation and Biological Activity of Guinea Pig DES-B-ASP30, DES-A-ASN21-Insulin." Canadian Journal of Biochemistry, 1976, vol. 54 pp. 866-871.
Baker et al, Philosophical Transactions of the Royal Society of London, 1988, vol. 319, pp. 369-456.
Ward et al., Bioessays, 2009, vol. 31, pp. 422-434.
Seino et al., Biochemical and Biophysical Research Communications, 1989, vol. 159, pp. 312-316.
Moller et al., Molecular Endocrinology, 1989, Vol. 3, No. 8, pp. 1263-1269.
Mosthaf et al., The EMBO Journal, 1990, vol. 9, pp. 2409-2413.
Yamaguchi et al., Endocrinology, 1991, vol. 129, No. 4, pp. 2058-2066.
Yamaguchi et al., Endocrinology, 1993, vol. 132, No. 3, pp. 1132-1138.
Blundell et al., Advances in Protein Chemistry, 1972, vol. 26, pp. 279-402.
Pullen et al., Nature, 1976, vol. 259, pp. 369-373.
Nakagawa et al., Journal of Biological Chemistry, 1987, vol. 262, No. 25, pp. 12054-12058.
Mirmira et al., The Journal of Biological Chemistry, 1991, vol. 266, No. 3, pp. 1428-1436.
Xu et al., Biochemistry, 2004, vol. 43, pp. 8356-8372.
De Meyts et al., Biochemical and Biophysical Research Communications, 1973, vol. 55, pp. 154-161.
Kurose et al., Journal of Biological Chemistry, 1994, vol. 269, No. 46, pp. 29190-29197.
Shoelson et al., Journal of Biological Chemistry, 1993, vol. 268, No. 6, pp. 4085-4091.
Zakova et al., Biochemistry, 2008, vol. 47, pp. 5858-5868.
Fischer et al., Biological Chemistry, 1985, vol. 366, pp. 521-525.
Hua et al., Nature, 1991, vol. 354, pp. 238-241.
Ludvigsen et al., Jouronal of Molecular Biology, 1998, vol. 279, pp. 1-7.
Nakagawa et al., Biochemistry, 1992, vol. 31, pp. 3204-3214.
Markussen et al., International Journal of Peptide and Protein Research, 1985, vol. 26, No. 1, pp. 70-77.
Shoelson et al., Nature, 1983, vol. 302, pp. 540-543.
Glendorf et al., Biochemistry, 2008, vol. 47, p. 4743-4751.
Soos et al., Biochemical Journal, 1986, vol. 235, No. 1, pp. 199-208.

(56) References Cited

OTHER PUBLICATIONS

Slaaby et al., Journal of Biological Chemistry, 2006, vol. 281, No. 36, pp. 25869-25874.
Volund, Biometrics, 1978, vol. 34, pp. 357-365.
Kabsch, Journal of Applied Crystallogrpahy, 1993, vol. 26, pp. 795-800.
Vagin et al., Journal of Applied Crystallography, 1997, vol. 30, pp. 1022-1025.
Murshudov, ACTA Crystallographica, 1997, vol. 53, pp. 240-255.
Emsley et al., ACTA Crystallographica, 2004, vol. 60, pp. 2126-2132.
Kjeldsen et al., Biotechnology and Genetic Engineering Reviews, 2001, vol. 18, pp. 89-121.
Schaffer, European Journal of Biochemistry, 1994, vol. 221, pp. 1127-1132.
Wells, Biochemistry, 1990, vol. 29, vol. 37, pp. 8509-8517.
Kaarsholm et al., Biochemistry, 1993, vol. 32, pp. 10773-10778.
Kristensen et al., Journal of Biological Chemistry, 2002, vol. 277, No. 21, pp. 18340-18345.
Mynarcik et al., Journal of Biological Chemistry, 1996, vol. 271, No. 5, pp. 2439-2442.
Whittaker, Journal of Biological Chemistry, 2005, vol. 280, No. 22, pp. 20932-20936.
Whittaker et al., Journal of Biological Chemistry, 2002, vol. 277, No. 49, pp. 47380-47384.
Frasca et al., Molecular and Cellular Biology, 1999, vol. 19, No. 5, pp. 3278-3288.
Kjeldsen et al., Proceedings of the National Academy of Sciences of the USA, 1991, vol. 88, No. 10, pp. 4404-4408.
Spoden M et al. International Journal of Peptide and Protein. "Structure-Function Relationships of DES-(B26-B30)-Insulin." 1995. vol. 46(3-4). pp. 221-227.
Chen, Y et al. Journal of Biological Chemistry. "In Vitro Refolding/Unfolding Pathways of Amphioxus Insulin-Like Peptide Implications for Folding Behavior of Insulin Family Proteins." 2004. vol. 279(53). pp. 55224-55233.
Chu Ying-Chi et al., "The A14 Position of Insulin Tolerates Considerable Structural Alterations with Modest Effects on the Biological Behavior of the Hormone," Journal of Protein Chemistry, 1992, vol. 11, No. 5, pp. 571-577.
Seabright, P.J. et al., "The Characterization of Endosomal Insulin Degradation Intermediates and their Sequence of Production," Biochemical Journal, 1996, vol. 320, No. 3, pp. 947-956.
Stentz, F.B. et al., "Identification of Insulin Intermediates and Sites of Cleavage of Native Insulin by Insulin Protease from Human Fibroblasts," Journal of Biological Chemistry, 1989, vol. 264, No. 34, pp. 20275-20282.
Smith, L.E, "Accession: P01337 1 [gi: 32172038] & Accession: P01337 2 [gi: 32172039], Definition: [Segment 1 of 2] Insulin-1 & [Segment 2 of 2] Insulin-1", NCBI Entrez Protein [online]; Mar. 21, 2006 uploaded, NCBI, [retrieved on Sep. 11, 2013], Retrieved from the internet:http://www.ncbi.nlm.nih.gov/protein/32172037?sat=34&satkey=10044352.
Aminlari et al., 1977, "Protein Dispersibility of Spray-Dried Whole Soybean Milk Base: Effect of Processing Variables," Journal of Food Science 42(4):985-988.
Bekerman et al., 2004, "Cyclosporin Nanoparticulate Liposheres for Oral Administration," Journal of Pharmaceutical Sciences 93(5):1264-1270.
Bennett et al., 2003, "Insulin Inhibition of the Proteasome Is Dependent on Degradation of Insulin by Insulin Degrading Enzyme," Journal of Endocrinology 177:399-405.
Bhatnagar et al., 2006, "Molecular Variants and Derivatives of Insulin for Improved Glycemic Control in Diabetes," Progress in Biophysics and Molecular Biology 91(3):199-228.
Chin et al., 1994, "Communication to the Editor: On Protein Solubility in Organic Solvents," Biotechnology and Bioengineering 44:140-145.

Foster et al., 1995, "Powder Characteristics of Proteins Spray-Dried From Different Spray-Driers," Drug Development and Industrial Pharmacy 21(15):1705-1723.
Hartmann et al., 1992, "Comparison of Subcutaneously Administered Soluble Insulin and Des-(B26-B30)-Insulin-B25-Amide in Rabbit, Pig and Healthy Man," Diabetes Research and Clinical Practice 16(3):175-181.
Hashimoto et al., 1989, "Synthesis of Palmitoyl Derivatives of Insulin and Their Biological Activities" Pharmaceutical Research 6(2):171-176.
Havelund et al., 2004, "The Mechanism of Protraction of Insulin Detemir, a Long-Acting, Acylated Analog of Human Insulin" Pharmaceutical Research 21(8):1498-1504.
Hinds et al., 2000, "Synthesis and Characterization of Poly(Ethylene Glycol)-Insulin Conjugates," Bioconjugate Chemistry 11(2):195-201.
Hinds et al., 2002, "Effects of Peg Conjugation on Insulin Properties," Advanced Drug Delivery Reviews 54 (4):505-530.
Iwamoto, 2000, "New Insulin Formulation," Annual Review Endocrine Metabolism pp. 46-53.
Jonassen et al., 2006, "Synthesis of Palmitoyl Derivatives of Insulin and Their Biological Activities," Pharmaceutical Research 23(1):49-55.
Kochendoerfer et al., 2003, "Design and Chemical Synthesis of a Homogenous Polymer-Modified Erythropoiesis Protein," Science 299:884-887.
Kurtz et al., 1983, "Circulating IgG Antibody to Protamine in Patients Treated with Protamine-Insulins," Diabetologia 25(2):322-324.
Markussen et al., 1987, "Soluble, Prolonged-Acting Insulin Derivatives. I. Degree of Protraction, Crystallizability of Insulins Substituted in The . . . " Protein Engineering 1(3):205-213.
Markussen et al., 1988, "Soluble, Prolonged-Acting Insulin Derivatives. III. Degree of Protraction, Crystallizability and Chemical Stability of Insulins Substituted in Positions A21, B13, B23, B27 and B30," Protein Engineering 2 (2):157-166.
Muranishi et al., 1992, "Trials of Lipid Modification of Peptide Hormones for Intestinal Delivery," Journal of Controlled Release 19:179-188.
Samuel et al., 1978, "Studies on the Immunogenicity of Protamines in Humans Andexperimental Animals by Means of a Micro-Complement Fixation Test," Clinical Experminemtal Immunology 33:252-260.
Schlichtkrull et al., 1956, "Insulin Crystals," Acta Chemica Scandinavica 10(9):1455-1458.
Toorisaka et al., 2004, "Emulsion-Based Drug Delivery Systems," Membrane 29(2):98-104 Abstract.
Uchio et al., 1999, "Site-Specific Insulin Conjugates With Enhanced Stability and Extended Action Profile," Advanced Drug Delivery Reviews 35:289-306.
Whittingham et al., 2004, "Crystallographic and Solution . . . " Biochemistry 43:5987-5995.
L. Schäffer et al, Assembly of high-affinity insulin receptor agonists and antagonists from peptide building blocks, Journal :Proceedings of the National Academy of Sciences of the United States of America, Year 2003, vol. 100, pp. 4435-4439.
L Schaffer et al, A novel high-affinity peptide antagonist to the insulin receptor.Journal: Biochemical and Biophysical Research Communications, Year 2008, vol. 376 , pp. 380-383.
Riebel, U. et al,Equivalent In Vivo Biological Activity of Insulin Analogues and Human Insulin Despite Different In Vitro Potencies, Journal :Diabetes, Year 1990,vol. 39, pp. 1033-1039.
Hinds, K D et al. Advanced Drugs Delivery Reviews. "Effects of Peg Conjugation on Insulin Properties." 2002. vol. 54. pp. 505-530.
Chu Ying-Chi et al. Journal of Protein Chemistry. "The A14 Position of Insulin Tolesrates Considerable Structural Alterations With Modest Effects on the Biological Behavior of the Hormone." 1992. vol. 11(5). pp. 571-577.
Database Geneseq [Online] May 7, 1992, "Modified human proinsulin with Gln A13 and Asp B17.", retrieved from EBI accession No. GSP:AAR20702 Database accession No. AAR20702.
Definition of hydrophobic and hydrophilic, Amino Acids, NJMS Department of Biochemistry and Molecular Biology. (http://njms2.umdnj.edu/biochweb/education/bioweb/PreK/AminoAcids.htm).

(56) References Cited

OTHER PUBLICATIONS

Hydrophobic Amino Acids, Molecular Cell Biology 6th edition (2008, W.H. Freeman and company) http://www.bio.miami.edu/tom/courses/protected/MCB6/ch02/2-14_part_1.jpg.

L. Schaffer et al, Assembly of high-affinity insulin receptor agonists and antagonists from peptide building blocks, Journal :Proceedings of the National Academy of Sciences of the United States of America, Year 2003, vol. 100, pp. 4435-4439.

* cited by examiner

SEQUENCE LISTING

<160> NUMBER OF SEQ ID NOS: 10

<210> SEQ ID NO 1
<211> LENGTH: 22
<212> TYPE: PRT
<213> ORGANISM: Artificial
<220> FEATURE:
<223> OTHER INFORMATION: Modified Insulin A chain
<220> FEATURE:
<221> NAME/KEY: MISC_FEATURE
<222> LOCATION: (8)..(8)
<223> OTHER INFORMATION: Xaa is Thr or His
<220> FEATURE:
<221> NAME/KEY: MISC_FEATURE
<222> LOCATION: (14)..(14)
<223> OTHER INFORMATION: Xaa is Asp, His, Lys, Arg, Pro, Gln or Glu
<220> FEATURE:
<221> NAME/KEY: MISC_FEATURE
<222> LOCATION: (15)..(15)
<223> OTHER INFORMATION: Xaa is Gln or Glu
<220> FEATURE:
<221> NAME/KEY: MISC_FEATURE
<222> LOCATION: (21)..(21)
<223> OTHER INFORMATION: Xaa is Asn, Gln, Gly or Ala
<220> FEATURE:
<221> NAME/KEY: MISC_FEATURE
<222> LOCATION: (22)..(22)
<223> OTHER INFORMATION: Xaa is absent or Lys

<400> SEQUENCE: 1

Gly Ile Val Glu Gln Cys Cys Xaa Ser Ile Cys Ser Leu Xaa Xaa Leu
1               5                   10                  15

Glu Asn Tyr Cys Xaa Xaa
            20

<210> SEQ ID NO 2
<211> LENGTH: 29
<212> TYPE: PRT
<213> ORGANISM: Artificial
<220> FEATURE:
<223> OTHER INFORMATION: Modified Insulin B chain
<220> FEATURE:
<221> NAME/KEY: MISC_FEATURE
<222> LOCATION: (3)..(3)
<223> OTHER INFORMATION: Xaa is Asn, Gln, Gly or Ala
<220> FEATURE:
<221> NAME/KEY: MISC_FEATURE
<222> LOCATION: (10)..(10)
<223> OTHER INFORMATION: Xaa is His, Glu or Asp
<220> FEATURE:
<221> NAME/KEY: MISC_FEATURE
<222> LOCATION: (16)..(16)
<223> OTHER INFORMATION: Xaa is Tyr, Asp, His or Glu
<220> FEATURE:
<221> NAME/KEY: MISC_FEATURE
<222> LOCATION: (22)..(22)
<223> OTHER INFORMATION: Xaa is absent, Arg or Lys
<220> FEATURE:
<221> NAME/KEY: MISC_FEATURE
<222> LOCATION: (24)..(24)
<223> OTHER INFORMATION: Xaa is absent, Phe, Gly or His
<220> FEATURE:
<221> NAME/KEY: MISC_FEATURE
<222> LOCATION: (25)..(25)
<223> OTHER INFORMATION: Xaa is absent, Phe, Asn, Ala or His
<220> FEATURE:
<221> NAME/KEY: MISC_FEATURE
<222> LOCATION: (26)..(26)
<223> OTHER INFORMATION: Xaa is absent, Tyr, Gly, Glu or Lys
<220> FEATURE:
<221> NAME/KEY: MISC_FEATURE
<222> LOCATION: (27)..(27)
<223> OTHER INFORMATION: Xaa is absent, Gly, Lys or Thr
<220> FEATURE:
<221> NAME/KEY: MISC_FEATURE

```
<222> LOCATION: (28)..(28)
<223> OTHER INFORMATION: Xaa is absent, Pro, Gly, His, Lys, Asp or Glu
<220> FEATURE:
<221> NAME/KEY: MISC_FEATURE
<222> LOCATION: (29)..(29)
<223> OTHER INFORMATION: Xaa is absent or Lys

<400> SEQUENCE: 2

Phe Val Xaa Gln His Leu Cys Gly Ser Xaa Leu Val Glu Ala Leu Xaa
1               5                   10                  15

Leu Val Cys Gly Glu Xaa Gly Xaa Xaa Xaa Xaa Xaa Xaa
            20                  25

<210> SEQ ID NO 3
<211> LENGTH: 22
<212> TYPE: PRT
<213> ORGANISM: Artificial
<220> FEATURE:
<223> OTHER INFORMATION: Modified Insulin A chain
<220> FEATURE:
<221> NAME/KEY: MISC_FEATURE
<222> LOCATION: (14)..(14)
<223> OTHER INFORMATION: Xaa is Asp, His, Lys, Arg, Pro, Gln or Glu
<220> FEATURE:
<221> NAME/KEY: MISC_FEATURE
<222> LOCATION: (15)..(15)
<223> OTHER INFORMATION: Xaa is Gln or Glu
<220> FEATURE:
<221> NAME/KEY: MISC_FEATURE
<222> LOCATION: (21)..(21)
<223> OTHER INFORMATION: Xaa is Asn, Gln, Gly or Ala
<220> FEATURE:
<221> NAME/KEY: MISC_FEATURE
<222> LOCATION: (22)..(22)
<223> OTHER INFORMATION: Xaa is absent or Lys

<400> SEQUENCE: 3

Gly Ile Val Glu Gln Cys Cys Thr Ser Ile Cys Ser Leu Xaa Xaa Leu
1               5                   10                  15

Glu Asn Tyr Cys Xaa Xaa
            20

<210> SEQ ID NO 4
<211> LENGTH: 29
<212> TYPE: PRT
<213> ORGANISM: Artificial
<220> FEATURE:
<223> OTHER INFORMATION: Modified Insulin B chain
<220> FEATURE:
<221> NAME/KEY: MISC_FEATURE
<222> LOCATION: (3)..(3)
<223> OTHER INFORMATION: Xaa is Asn, Gln, Gly or Ala
<220> FEATURE:
<221> NAME/KEY: MISC_FEATURE
<222> LOCATION: (16)..(16)
<223> OTHER INFORMATION: Xaa is Tyr, Asp, His or Glu
<220> FEATURE:
<221> NAME/KEY: MISC_FEATURE
<222> LOCATION: (22)..(22)
<223> OTHER INFORMATION: Xaa is absent, Arg or Lys
<220> FEATURE:
<221> NAME/KEY: MISC_FEATURE
<222> LOCATION: (24)..(24)
<223> OTHER INFORMATION: Xaa is absent, Phe, Gly or His
<220> FEATURE:
<221> NAME/KEY: MISC_FEATURE
<222> LOCATION: (25)..(25)
<223> OTHER INFORMATION: Xaa is absent, Phe, Asn, Ala or His
<220> FEATURE:
<221> NAME/KEY: MISC_FEATURE
<222> LOCATION: (26)..(26)
<223> OTHER INFORMATION: Xaa is absent, Tyr, Gly, Glu or Lys
<220> FEATURE:
```

```
<221> NAME/KEY: MISC_FEATURE
<222> LOCATION: (27)..(27)
<223> OTHER INFORMATION: Xaa is absent, Gly, Lys or Thr
<220> FEATURE:
<221> NAME/KEY: MISC_FEATURE
<222> LOCATION: (28)..(28)
<223> OTHER INFORMATION: Xaa is absent, Pro, Gly, His, Lys, Asp or Glu
<220> FEATURE:
<221> NAME/KEY: MISC_FEATURE
<222> LOCATION: (29)..(29)
<223> OTHER INFORMATION: Xaa is absent or Lys

<400> SEQUENCE: 4

Phe Val Xaa Gln His Leu Cys Gly Ser His Leu Val Glu Ala Leu Xaa
1               5                   10                  15

Leu Val Cys Gly Glu Xaa Gly Xaa Xaa Xaa Xaa Xaa
            20                  25

<210> SEQ ID NO 5
<211> LENGTH: 22
<212> TYPE: PRT
<213> ORGANISM: Artificial
<220> FEATURE:
<223> OTHER INFORMATION: Modified Insulin A chain
<220> FEATURE:
<221> NAME/KEY: MISC_FEATURE
<222> LOCATION: (14)..(14)
<223> OTHER INFORMATION: Xaa is Asp, His, Lys, Arg, Pro, Gln or Glu
<220> FEATURE:
<221> NAME/KEY: MISC_FEATURE
<222> LOCATION: (21)..(21)
<223> OTHER INFORMATION: Xaa is Asn, Gln, Gly or Ala
<220> FEATURE:
<221> NAME/KEY: MISC_FEATURE
<222> LOCATION: (22)..(22)
<223> OTHER INFORMATION: Xaa is absent or Lys

<400> SEQUENCE: 5

Gly Ile Val Glu Gln Cys Cys Thr Ser Ile Cys Ser Leu Xaa Gln Leu
1               5                   10                  15

Glu Asn Tyr Cys Xaa Xaa
            20

<210> SEQ ID NO 6
<211> LENGTH: 29
<212> TYPE: PRT
<213> ORGANISM: Artificial
<220> FEATURE:
<223> OTHER INFORMATION: Modified Insulin B chain
<220> FEATURE:
<221> NAME/KEY: MISC_FEATURE
<222> LOCATION: (3)..(3)
<223> OTHER INFORMATION: Xaa is Asn, Gln, Gly or Ala
<220> FEATURE:
<221> NAME/KEY: MISC_FEATURE
<222> LOCATION: (16)..(16)
<223> OTHER INFORMATION: Xaa is Tyr, Asp, His or Glu
<220> FEATURE:
<221> NAME/KEY: MISC_FEATURE
<222> LOCATION: (24)..(24)
<223> OTHER INFORMATION: Xaa is absent, Phe, Gly or His
<220> FEATURE:
<221> NAME/KEY: MISC_FEATURE
<222> LOCATION: (25)..(25)
<223> OTHER INFORMATION: Xaa is absent, Phe, Asn, Ala or His
<220> FEATURE:
<221> NAME/KEY: MISC_FEATURE
<222> LOCATION: (26)..(26)
<223> OTHER INFORMATION: Xaa is absent, Tyr, Gly, Glu or Lys
<220> FEATURE:
<221> NAME/KEY: MISC_FEATURE
<222> LOCATION: (27)..(27)
<223> OTHER INFORMATION: Xaa is absent, Gly, Lys or Thr
```

```
<220> FEATURE:
<221> NAME/KEY: MISC_FEATURE
<222> LOCATION: (28)..(28)
<223> OTHER INFORMATION: Xaa is absent, Pro, Gly, His, Lys, Asp or Glu
<220> FEATURE:
<221> NAME/KEY: MISC_FEATURE
<222> LOCATION: (29)..(29)
<223> OTHER INFORMATION: Xaa is absent or Lys

<400> SEQUENCE: 6

Phe Val Xaa Gln His Leu Cys Gly Ser His Leu Val Glu Ala Leu Xaa
1               5                   10                  15

Leu Val Cys Gly Glu Arg Gly Xaa Xaa Xaa Xaa Xaa Xaa
            20                  25

<210> SEQ ID NO 7
<211> LENGTH: 22
<212> TYPE: PRT
<213> ORGANISM: Artificial
<220> FEATURE:
<223> OTHER INFORMATION: Modified Insulin A chain
<220> FEATURE:
<221> NAME/KEY: MISC_FEATURE
<222> LOCATION: (14)..(14)
<223> OTHER INFORMATION: Xaa is Asp, His, Lys, Arg, Pro or Glu
<220> FEATURE:
<221> NAME/KEY: MISC_FEATURE
<222> LOCATION: (22)..(22)
<223> OTHER INFORMATION: Xaa is absent or Lys

<400> SEQUENCE: 7

Gly Ile Val Glu Gln Cys Cys Thr Ser Ile Cys Ser Leu Xaa Gln Leu
1               5                   10                  15

Glu Asn Tyr Cys Asn Xaa
            20

<210> SEQ ID NO 8
<211> LENGTH: 29
<212> TYPE: PRT
<213> ORGANISM: Artificial
<220> FEATURE:
<223> OTHER INFORMATION: Modified Insulin B chain
<220> FEATURE:
<221> NAME/KEY: MISC_FEATURE
<222> LOCATION: (16)..(16)
<223> OTHER INFORMATION: Xaa is Tyr, Asp, His or Glu
<220> FEATURE:
<221> NAME/KEY: MISC_FEATURE
<222> LOCATION: (24)..(24)
<223> OTHER INFORMATION: Xaa is Phe or His
<220> FEATURE:
<221> NAME/KEY: MISC_FEATURE
<222> LOCATION: (25)..(25)
<223> OTHER INFORMATION: Xaa is Phe or His
<220> FEATURE:
<221> NAME/KEY: MISC_FEATURE
<222> LOCATION: (26)..(26)
<223> OTHER INFORMATION: Xaa is Tyr, Gly or Glu
<220> FEATURE:
<221> NAME/KEY: MISC_FEATURE
<222> LOCATION: (27)..(27)
<223> OTHER INFORMATION: Xaa is absent, Gly, Lys or Thr
<220> FEATURE:
<221> NAME/KEY: MISC_FEATURE
<222> LOCATION: (28)..(28)
<223> OTHER INFORMATION: Xaa is absent, Pro, Gly, His, Lys, Asp or Glu
<220> FEATURE:
<221> NAME/KEY: MISC_FEATURE
<222> LOCATION: (29)..(29)
<223> OTHER INFORMATION: Xaa is absent or Lys

<400> SEQUENCE: 8
```

```
Phe Val Asn Gln His Leu Cys Gly Ser His Leu Val Glu Ala Leu Xaa
1               5                   10                  15

Leu Val Cys Gly Glu Arg Gly Xaa Xaa Xaa Xaa Xaa Xaa
            20                  25

<210> SEQ ID NO 9
<211> LENGTH: 21
<212> TYPE: PRT
<213> ORGANISM: Artificial
<220> FEATURE:
<223> OTHER INFORMATION: Modified Insulin A chain
<220> FEATURE:
<221> NAME/KEY: MISC_FEATURE
<222> LOCATION: (14)..(14)
<223> OTHER INFORMATION: Xaa is Asp, His, Lys, Arg, Pro, Gln or Glu

<400> SEQUENCE: 9

Gly Ile Val Glu Gln Cys Cys Thr Ser Ile Cys Ser Leu Xaa Gln Leu
1               5                   10                  15

Glu Asn Tyr Cys Asn
            20

<210> SEQ ID NO 10
<211> LENGTH: 29
<212> TYPE: PRT
<213> ORGANISM: Artificial
<220> FEATURE:
<223> OTHER INFORMATION: Modified Insulin B chain
<220> FEATURE:
<221> NAME/KEY: MISC_FEATURE
<222> LOCATION: (24)..(24)
<223> OTHER INFORMATION: Xaa is Phe or His
<220> FEATURE:
<221> NAME/KEY: MISC_FEATURE
<222> LOCATION: (25)..(25)
<223> OTHER INFORMATION: Xaa is Phe or His
<220> FEATURE:
<221> NAME/KEY: MISC_FEATURE
<222> LOCATION: (26)..(26)
<223> OTHER INFORMATION: Xaa is Tyr, Gly, Glu or Lys
<220> FEATURE:
<221> NAME/KEY: MISC_FEATURE
<222> LOCATION: (27)..(27)
<223> OTHER INFORMATION: Xaa is absent, Gly, Lys or Thr
<220> FEATURE:
<221> NAME/KEY: MISC_FEATURE
<222> LOCATION: (28)..(28)
<223> OTHER INFORMATION: Xaa is absent, Pro, Gly, His, Lys, Asp or Glu
<220> FEATURE:
<221> NAME/KEY: MISC_FEATURE
<222> LOCATION: (29)..(29)
<223> OTHER INFORMATION: Xaa is absent or Lys

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Xaa Xaa Xaa Xaa Xaa Xaa
            20                  25
```

PROTEASE-STABILIZED INSULIN ANALOGUES

CROSS-REFERENCE TO RELATED APPLICATIONS

This application is a 35 U.S.C. §371 national stage application of International Patent Application PCT/EP2009/053019 (published as WO 2009/112583), filed Mar. 13, 2009, which claimed priority of European Patent Application 08102598.3, filed Mar. 14, 2008; this application further claims priority under 35 U.S.C. §119 of U.S. Provisional Application 61/037,429, filed Mar. 18, 2008.

FIELD OF THE INVENTION

The present invention relates to novel insulin analogues exhibiting resistance towards protease, a method for the preparation of such insulin analogues, insulin preparations containing the insulin analogues of the invention and a method of treating diabetes mellitus using these insulin analogues.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jul. 30, 2010. The Sequence Listing is made up of 9 kilobytes, and the information contained in the attached "SEQUENCE LISTING" is identical to the information in the specification as originally filed. No new matter is added.

BACKGROUND OF THE INVENTION

Diabetes mellitus is a metabolic disorder in which the ability to utilize glucose is partly or completely lost. About 5% of all people suffer from diabetes and the disorder approaches epidemic proportions.

Human insulin consists of two polypeptide chains, the A and B chains which contain 21 and 30 amino acid residues, respectively. The A and B chains are interconnected by two disulphide bridges. Insulin from most other species is similar, but may contain amino acid substitutions in some positions. In the treatment of diabetes mellitus, many varieties of insulin formulations have been suggested and used, such as regular insulin, isophane insulin (designated NPH), insulin zinc suspensions (such as SEMILENTE®, LENTE®, and ULTRALENTE®), and biphasic isophane insulin. Also human insulin analogues have been developed. They are designed for particular profiles of action, i.e. fast acting or prolonged action. Commercially available products comprising such insulin analogues include LEVEMIR®, NOVORAPID®, HUMALOG®, APIDRA® and LANTUS®.

Normally, insulin formulations are administered by subcutaneous injection.

However, administration by the oral route would be advantageous due to patient compliance, safety and convenience.

Oral administration of protein drugs such as insulin often results in very low bioavailability due to several barriers such as enzymatic degradation in the gastrointestinal (GI) tract, drug efflux pumps, insufficient and variable absorption from the intestinal mucosa, as well as first pass metabolism in the liver. Human insulin is degraded by various digestive enzymes found in the stomach (pepsin and gastricsin), in the intestinal lumen (chymotrypsin, trypsin, elastase, carboxypeptidases, etc.) and in mucosal surfaces of the GI tract (aminopeptidases, carboxypeptidases, enteropeptidases, dipeptidyl peptidases, endopeptidases, etc.). Recent formulation designs for oral protein/peptide delivery include co-formulations with protease inhibitors, permeation enhancers, polymer-based delivery systems and insulin conjugates. The latter includes hexyl-insulin-monoconjugate-2 (HIM2) (Nobex Cooperation and GSK), a human insulin analogue with a PEG 7-hexyl group attached to B29. In for example U.S. Pat. No. 7,030,082, U.S. Pat. No. 6,867,183 and U.S. Pat. No. 6,770,625 oral HIM2 has been reported to have increased proteolytic stability and bioavailability compared to insulin.

Combination of a protease resistant insulin analogue with an oral protein delivery system represents a promising strategy for oral insulin administration. Furthermore no enzyme inhibitors need to be incorporated in the delivery system.

SUMMARY OF THE INVENTION

The present invention relates to insulin analogues with enhanced proteolytic stability and retained biological insulin activity.

In one embodiment an insulin analogue is provided wherein
the A-chain of the insulin analogue comprises at least one mutation relative to the parent insulin, wherein one mutation is in position A14 which is substituted to an amino acid selected from the group consisting of Lys, Glu, Arg, Asp, Pro, Gln and His; and
the B-chain of the insulin analogue comprises at least two mutations relative to the parent insulin, wherein two or more mutations are in the form of deletions of the amino acids in positions B27, B28, B29 and B30, or a combination of a deletion of the amino acid in position B30 and a substitution of an amino acid selected from the amino acid substitutions in position: B24 to Gly or His, B25 to His, B26 to Gly, Glu or Lys, B27 to Gly, Glu or Lys and B28 to Asp, His, Gly, Lys or Glu;
which is selected from the group consisting of:
A8H, A14E, A22K, B16H, B25H, B29R, desB30 human insulin
A8H, A14E, A22K, B25H, B29R, desB30 human insulin
A8H, A14E, B10E, B25H, B26G, B27G, B28G, desB30 human insulin
A8H, A14E, B16H, B25H, desB30 human insulin
A8H, A14E, B22K, B25H, B29R, desB30 human insulin
A8H, A14H, A22K, B16H, B25H, B29R, desB30 human insulin
A8H, A14H, B16H, B25H, desB30 human insulin
A14E, B16H, desB27, desB28, desB29, desB30 human insulin
A14E, B16E, desB27, desB28, desB29, desB30 human insulin
A14E, B16D, desB27, desB28, desB29, desB30 human insulin
A14E, B24G, desB30 human insulin
A14E, B28E, desB29, desB30 human insulin
A14E, B28E, desB30 human insulin
A14E, B28H, desB30 human insulin
A14E, desB1, desB2, desB3, B25H, B27K, desB28, desB29, desB30 human insulin
A14E, desB27, desB28, desB29, desB30 human insulin
A14P, B25H, desB30 human insulin
A21G, desB27, desB30 human insulin
B27K, desB28, desB29, desB30 human insulin A14D, B25H, desB27, desB28, desB29, desB30 human insulin,
A14E, A15E, B25H, desB30 human insulin
A14E, A18Q, A21G, B3Q, B25H, B27E, desB30 human insulin
A14E, A21G, B25H, desB27, desB30 human insulin
A14E, A21G, B25H, desB30 human insulin
A14E, A22K, B16E, B25H, B29R, desB30 human insulin
A14E, A22K, B16H, B25H, B29R, desB30 human insulin
A14E, A22K, B25H, B26G, B27G, B28G, B29R, desB30 human insulin
A14E, A22K, B25H, B27E, B29R, desB30 human insulin
A14E, B10E, B25H, B26G, B27G, B28G, desB30 human insulin
A14E, B16D, B25H, desB27, desB28, desB29, desB30 human insulin
A14E, B16E, B22K, B25H, B29R, desB30 human insulin
A14E, B16E, B25H, desB27, desB28, desB29, desB30 human insulin
A14E, B16H, B22K, B25H, B29R, desB30 human insulin
A14E, B16H, B25H, desB27, desB28, desB29, desB30 human insulin
A14E, B22K, B25H, B26G, B27G, B28G, B29R, desB30 human insulin
A14E, B24G, B25H, desB30 human insulin
A14E, B25H, B26E, B27E, desB30 human insulin
A14E, B25H, B26G, B27E, B28G, desB30 human insulin
A14E, B25H, B26G, B27G B28K, desB29, desB30 human insulin
A14E, B25H, B26G, B27G, desB30 human insulin
A14E, B25H, B26G, B27K, desB28, desB29, desB30 human insulin
A14E, B25H, B26G, B27T, B28G, desB30 human insulin
A14E, B25H, B26G, desB30 human insulin
A14E, B25H, B27G, B28G, desB30 human insulin
A14E, B25H, B27G, desB30 human insulin
A14E, B25H, B28G, desB30 human insulin
A14E, B25H, B29R, desB30 human insulin
A14H, B16H, B24H, B25H, B26G, B27G, B28G, desB30 human insulin
A14H, B16H, B24H, B25H, desB27, desB28, desB29, desB30 human insulin
A14H, B16H, B25H, desB27, desB28, desB29, desB30 human insulin
A14H, B24H, B25H, B26G, B27G, B28G, desB30 human insulin
A14E, A22K, B16H, B25H, B29R, desB30 human insulin
A14E, A22K, B16E, B25H, B29R, desB30 human insulin
A14E, A22K, B16H, B25H, desB27, B29R, desB30 human insulin
A14E, A22K, B16E, B25H, desB27, B29R, desB30 human insulin
A14E, A22K, B25H, B27E, B29R, desB30 human insulin
A14E, A22K, B16H, B25H, B27E, B29R, desB30 human insulin
A14E, A22K, B16E, B25H, B27E, B29R, desB30 human insulin
A14E, A22K, B25H, B26G, B27G, B28G, B29R, desB30 human insulin
A14E, A22K, B16H, B25H, B26G, B27G, B28G, B29R, desB30 human insulin
A14E, A22K, B16E, B25H, B26G, B27G, B28G, B29R, desB30 human insulin
A14E, A22K, B16E, B25H, B26G, B27E, B28G, B29R, desB30 human insulin
A14E, A22K, B16E, B25H, B26G, B27E, B28G, B29R, desB30 human insulin
A14E, A22K, B16H, B25H, desB30 human insulin
A14E, A22K, B16E, B25H, desB30 human insulin
A14E, A22K, B25H, B27E, desB30 human insulin
A14E, A22K, B16H, B25H, B27E, desB30 human insulin
A14E, A22K, B16E, B25H, B27E, desB30 human insulin
A14E, A22K, B25H, B26G, B27G, B28G, desB30 human insulin
A14E, A22K, B16H, B25H, B26G, B27G, B28G, desB30 human insulin
A14E, A22K, B16E, B25H, B26G, B27G, B28G, desB30 human insulin
A14E, A22K, B16E, B25H, B26G, B27E, B28G, desB30 human insulin
A14E, A22K, B16H, B25H, B26G, B27E, B28G, desB30 human insulin
A14E, A22K, B16H, B25H, desB27, desB30 human insulin
A14E, A22K, B16E, B25H, desB27, desB30 human insulin
A14Q, A22K, B16H, B25H, B29R, desB30 human insulin
A14Q, A22K, B16E, B25H, B29R, desB30 human insulin
A14Q, A22K, B16H, B25H, desB27, B29R, desB30 human insulin
A14Q, A22K, B16E, B25H, desB27, B29R, desB30 human insulin
A14Q, A22K, B25H, B27E, B29R, desB30 human insulin
A14Q, A22K, B16H, B25H, B27E, B29R, desB30 human insulin
A14Q, A22K, B16E, B25H, B27E, B29R, desB30 human insulin
A14Q, A22K, B25H, B26G, B27G, B28G, B29R, desB30 human insulin
A14Q, A22K, B16H, B25H, B26G, B27G, B28G, B29R, desB30 human insulin
A14Q, A22K, B16E, B25H, B26G, B27G, B28G, B29R, desB30 human insulin
A14Q, A22K, B16E, B25H, B26G, B27E, B28G, B29R, desB30 human insulin
A14Q, A22K, B16H, B25H, B26G, B27E, B28G, B29R, desB30 human insulin
A14Q, A22K, B16H, B25H, desB30 human insulin
A14Q, A22K, B16E, B25H, desB30 human insulin
A14Q, A22K, B25H, B27E, desB30 human insulin
A14Q, A22K, B16H, B25H, B27E, desB30 human insulin
A14Q, A22K, B16E, B25H, B27E, desB30 human insulin
A14Q, A22K, B25H, B26G, B27G, B28G, desB30 human insulin
A14Q, A22K, B16H, B25H, B26G, B27G, B28G, desB30 human insulin
A14Q, A22K, B16E, B25H, B26G, B27G, B28G, desB30 human insulin
A14Q, A22K, B16E, B25H, B26G, B27E, B28G, desB30 human insulin
A14Q, A22K, B16H, B25H, B26G, B27E, B28G, desB30 human insulin
A14Q, A22K, B16H, B25H, desB27, desB30 human insulin
A14Q, A22K, B16E, B25H, desB27, desB30 human insulin
A14P, A22K, B16H, B25H, B29R, desB30 human insulin
A14P, A22K, B16E, B25H, B29R, desB30 human insulin
A14P, A22K, B16H, B25H, desB27, B29R, desB30 human insulin
A14P, A22K, B16E, B25H, desB27, B29R, desB30 human insulin
A14P, A22K, B25H, B27E, B29R, desB30 human insulin
A14P, A22K, B16H, B25H, B27E, B29R, desB30 human insulin
A14P, A22K, B16E, B25H, B27E, B29R, desB30 human insulin A14P, A22K, B25H, B26G, B27G, B28G, B29R, desB30 human insulin
A14P, A22K, B16H, B25H, B26G, B27G, B28G, B29R, desB30 human insulin
A14P, A22K, B16E, B25H, B26G, B27G, B28G, B29R, desB30 human insulin
A14P, A22K, B16E, B25H, B26G, B27E, B28G, B29R, desB30 human insulin
A14P, A22K, B16H, B25H, B26G, B27E, B28G, B29R, desB30 human insulin
A14P, A22K, B16H, B25H, desB30 human insulin
A14P, A22K, B16E, B25H, desB30 human insulin
A14P, A22K, B25H, B27E, desB30 human insulin
A14P, A22K, B16H, B25H, B27E, desB30 human insulin
A14P, A22K, B16E, B25H, B27E, desB30 human insulin
A14P, A22K, B25H, B26G, B27G, B28G, desB30 human insulin
A14P, A22K, B16H, B25H, B26G, B27G, B28G, desB30 human insulin
A14P, A22K, B16E, B25H, B26G, B27G, B28G, desB30 human insulin
A14P, A22K, B16E, B25H, B26G, B27E, B28G, desB30 human insulin
A14P, A22K, B16H, B25H, B26G, B27E, B28G, desB30 human insulin
A14P, A22K, B16H, B25H, desB27, desB30 human insulin
A14P, A22K, B16E, B25H, desB27, desB30 human insulin
A14D, A22K, B16H, B25H, B29R, desB30 human insulin
A14D, A22K, B16E, B25H, B29R, desB30 human insulin
A14D, A22K, B16H, B25H, desB27, B29R, desB30 human insulin
A14D, A22K, B16E, B25H, desB27, B29R, desB30 human insulin
A14D, A22K, B25H, B27E, B29R, desB30 human insulin
A14D, A22K, B16H, B25H, B27E, B29R, desB30 human insulin
A14D, A22K, B16E, B25H, B27E, B29R, desB30 human insulin
A14D, A22K, B25H, B26G, B27G, B28G, B29R, desB30 human insulin
A14D, A22K, B16H, B25H, B26G, B27G, B28G, B29R, desB30 human insulin
A14D, A22K, B16E, B25H, B26G, B27G, B28G, B29R, desB30 human insulin
A14D, A22K, B16E, B25H, B26G, B27E, B28G, B29R, desB30 human insulin
A14D, A22K, B16H, B25H, B26G, B27E, B28G, B29R, desB30 human insulin
A14D, A22K, B16H, B25H, desB30 human insulin
A14D, A22K, B16E, B25H, desB30 human insulin
A14D, A22K, B25H, B27E, desB30 human insulin
A14D, A22K, B16H, B25H, B27E, desB30 human insulin
A14D, A22K, B16E, B25H, B27E, desB30 human insulin
A14D, A22K, B25H, B26G, B27G, B28G, desB30 human insulin
A14D, A22K, B16H, B25H, B26G, B27G, B28G, desB30 human insulin
A14D, A22K, B16E, B25H, B26G, B27G, B28G, desB30 human insulin
A14D, A22K, B16E, B25H, B26G, B27E, B28G, desB30 human insulin
A14D, A22K, B16H, B25H, B26G, B27E, B28G, desB30 human insulin
A14D, A22K, B16H, B25H, desB27, desB30 human insulin
A14D, A22K, B16E, B25H, desB27, desB30 human insulin
A14E, A22K, B16H, B25H, desB27, B29R, desB30 human insulin
A14E, A22K, B16E, B25H, desB27, B29R, desB30 human insulin
A14E, A22K, B16H, B25H, desB27, desB30 human insulin
A14E, A22K, B16E, B25H, desB27, desB30 human insulin
A14E, B16H, B25H, desB27, desB30 human insulin
A14E, B16E, B25H, desB27, desB30 human insulin
A14P, A22K, B16H, B25H, desB27, B29R, desB30 human insulin
A14P, A22K, B16E, B25H, desB27, B29R, desB30 human insulin
A14P, A22K, B16H, B25H, desB27, desB30 human insulin
A14P, A22K, B16E, B25H, desB27, desB30 human insulin
A14P, B16H, B25H, desB27, desB30 human insulin
A14P, B16E, B25H, desB27, desB30 human insulin
A14D, A22K, B16H, B25H, desB27, B29R, desB30 human insulin
A14D, A22K, B16E, B25H, desB27, B29R, desB30 human insulin
A14D, A22K, B16H, B25H, desB27, desB30 human insulin
A14D, A22K, B16E, B25H, desB27, desB30 human insulin
A14D, B16H, B25H, desB27, desB30 human insulin
A14D, B16E, B25H, desB27, desB30 human insulin
A14Q, A22K, B16H, B25H, desB27, B29R, desB30 human insulin
A14Q, A22K, B16E, B25H, desB27, B29R, desB30 human insulin
A14Q, A22K, B16H, B25H, desB27, desB30 human insulin
A14Q, A22K, B16E, B25H, desB27, desB30 human insulin
A14Q, B16H, B25H, desB27, desB30 human insulin
A14Q, B16E, B25H, desB27, desB30 human insulin In another embodiment an insulin analogue is provided comprising an A-chain amino acid sequence of formula 9:

Formula (9)(SEQ ID No: 9)
Gly-Ile-Val-Glu-Gln-Cys-Cys-Thr-Ser-Ile-Cys-Ser-Leu-Xaa$_{A14}$-Gln-Leu-Glu-Asn-Tyr-Cys-Asn and a B-chain amino acid sequence of formula 10:

Formula (10)(SEQ ID No: 10)
Phe-Val-Asn-Gln-His-Leu-Cys-Gly-Ser-His-Leu-Val-Glu-Ala-Leu-Tyr-Leu-Val-Cys-Gly-Glu-Arg-Gly-Xaa$_{B24}$-Xaa$_{B25}$-Xaa$_{B26}$-Xaa$_{B27}$-Xaa$_{B28}$-Xaa$_{B29}$ wherein
Xaa$_{A14}$ is independently selected from Asp, His, Lys, Arg, Pro, Glu and Gln;
Xaa$_{B24}$ is independently selected from Phe, Gly and His;
Xaa$_{B25}$ is independently selected from Phe and His;
Xaa$_{B26}$ is independently selected from Tyr, Gly, Glu and Lys;
Xaa$_{B27}$ is absent or independently selected from Gly, Lys or Thr;
Xaa$_{B28}$ is absent or independently selected from Pro, Gly, His, Lys, Asp and Glu;
Xaa$_{B29}$ is absent or Lys;
the C-terminal may optionally be derivatized as an amide;
wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge;

wherein the A-chain of the insulin analogue comprises at least one mutation relative to the parent insulin and the B-chain of the insulin analogue comprises at least two mutations relative to the parent insulin; and wherein, if the mutations in the B-chain of the insulin analogue consist of the combination of a deletion of the amino acid in position B30 and a substitution of the amino acid in position B25 to His, then the at least one mutation in position A14 in the A-chain of the insulin analogue is selected from the group consisting of Lys, Arg and Pro.

In yet another embodiment a pharmaceutical composition is provided comprising a biologically active amount of the insulin analogue according to the invention and a pharmaceutically acceptable carrier.

Also a method for the treatment of diabetes mellitus in a subject and/or for reducing the blood glucose level in mammals comprising administering to a subject or mammal an insulin analogue or pharmaceutical composition according to the invention is provided.

DESCRIPTION OF THE INVENTION

In one embodiment of the invention insulin analogues with enhanced proteolytic stability and retained biological insulin activity are provided.

Several insulin analogues with improved stability towards digestive proteases have been identified by the inventors. These insulin analogues may be used in oral diabetes treatment due to increased bioavailability in the stomach or GI tract as a result of the enhanced resistance to proteolytic degradation when compared to unmodified human insulin.

Proteolytic stability of insulin analogues may be characterized by HPLC analysis of digests using human insulin, various insulin analogues, digestive enzymes and extracts (stomach, intestine and pancreas). The insulin analogues may be generated by recombinant expression and mutation or by chemical synthesis.

In one embodiment insulin analogues according to the invention exhibit increased half-lives in the presence of pepsin compared to human insulin.

In one embodiment an insulin analogue according to the invention is selected from the group consisting of:
A8H, A14E, A22K, B16H, B25H, B29R, desB30 human insulin
A8H, A14E, A22K, B25H, B29R, desB30 human insulin
A8H, A14E, B10E, B25H, B26G, B27G, B28G, desB30 human insulin
A8H, A14E, B16H, B25H, desB30 human insulin
A8H, A14E, B22K, B25H, B29R, desB30 human insulin
A8H, A14H, A22K, B16H, B25H, B29R, desB30 human insulin
A8H, A14H, B16H, B25H, desB30 human insulin
A14D, B25H, desB27, desB28, desB29, desB30 human insulin,
A14E, A15E, B25H, desB30 human insulin
A14E, A18Q, A21G, B3Q, B25H, B27E, desB30 human insulin
A14E, A21G, B25H, desB27, desB30 human insulin
A14E, A21G, B25H, desB30 human insulin
A14E, A22K, B16E, B25H, B29R, desB30 human insulin
A14E, A22K, B16H, B25H, B29R, desB30 human insulin
A14E, A22K, B25H, B26G, B27G, B28G, B29R, desB30 human insulin
A14E, A22K, B25H, B27E, B29R, desB30 human insulin
A14E, B10E, B25H, B26G, B27G, B28G, desB30 human insulin
A14E, B16D, B25H, desB27, desB28, desB29, desB30 human insulin
A14E, B16D, desB27, desB28, desB29, desB30 human insulin
A14E, B16E, B22K, B25H, B29R, desB30 human insulin
A14E, B16E, B25H, desB27, desB28, desB29, desB30 human insulin
A14E, B16E, desB27, desB28, desB29, desB30 human insulin
A14E, B16H, B22K, B25H, B29R, desB30 human insulin
A14E, B16H, B25H, desB27, desB28, desB29, desB30 human insulin
A14E, B16H, desB27, desB28, desB29, desB30 human insulin
A14E, B22K, B25H, B26G, B27G, B28G, B29R, desB30 human insulin
A14E, B24G, B25H, desB30 human insulin
A14E, B24G, B25H, desB30 human insulin
A14E, B24G, desB30 human insulin
A14E, B25H, B26E, B27E, desB30 human insulin
A14E, B25H, B26G, B27E, B28G, desB30 human insulin
A14E, B25H, B26G, B27G B28K, desB29, desB30 human insulin
A14E, B25H, B26G, B27G, desB30 human insulin
A14E, B25H, B26G, B27K, desB28, desB29, desB30 human insulin
A14E, B25H, B26G, B27T, B28G, desB30 human insulin
A14E, B25H, B26G, desB30 human insulin
A14E, B25H, B27G, B28G, desB30 human insulin
A14E, B25H, B27G, desB30 human insulin
A14E, B25H, B28G, desB30 human insulin
A14E, B25H, B29R, desB30 human insulin
A14E, B28E, desB29, desB30 human insulin
A14E, B28E, desB30 human insulin
A14E, B28H, desB30 human insulin
A14E, desB1, desB2, desB3, B25H, B27K, desB28, desB29, desB30 human insulin
A14E, desB27, desB28, desB29, desB30 human insulin
A14H, B16H, B24H, B25H, B26G, B27G, B28G, desB30 human insulin
A14H, B16H, B24H, B25H, desB27, desB28, desB29, desB30 human insulin
A14H, B16H, B25H, desB27, desB28, desB29, desB30 human insulin
A14H, B24H, B25H, B26G, B27G, B28G, desB30 human insulin
A14P, B25H, desB30 human insulin
A21G, desB27, desB30 human insulin
B27K, desB28, desB29, desB30 human insulin In another embodiment an insulin analogue according to the invention is selected from the group consisting of:
desB27, desB28, desB29, desB30 human insulin
desB27, desB30 human insulin
desB28, desB29, desB30 human insulin
B24H, B25H, desB27, desB28, desB29, desB30 human insulin
B24H, B25H, B26G, B27G, B28G, desB30 human insulin
B24G, B25H, desB30 human insulin
B24G, desB30 human insulin
B25H, desB26, desB27, desB28, desB29, desB30 human insulin
B25H, desB27, desB28, desB29, desB30 human insulin
B25H, desB27, desB30 human insulin
B25H, B27K, desB28, desB29, desB30 human insulin
B25H, B26E, B27E, desB30 human insulin
B25H, B26G, desB27, desB28, desB29, desB30 human insulin B25H, B26G, B27K, desB28, desB29, desB30 human insulin
B25H, B26G, B27G, desB28, desB29, desB30 human insulin
B25H, B26G, B27G, B28K, desB29, desB30 human insulin
B25H, B26G, B27G, B28G, desB29, desB30 human insulin
B25H, B26G, B27G, B28G, B29K, desB30 human insulin
B25H, B26G, B27E, B28G, desB30 human insulin
B25H, B26G, B27T, B28G, desB30 human insulin
B25H, B26G, B27G, B28G, B29R, desB30 human insulin
B25H, B26G, B27G, B28G, desB30 human insulin
B25H, B26G, B27G, desB30 human insulin
B25H, B26G, desB30 human insulin
B25H, B27E, B29R, desB30 human insulin
B25H, B27E, B29R, desB30 human insulin
B25H, B27E, desB30 human insulin
B25H, B27G, desB28, desB29, desB30 human insulin
B25H, B27K, desB28, desB29, desB30 human insulin
B25H, B27G, B28K, desB29, desB30 human insulin
B25H, B27G, B28G, desB29, desB30 human insulin
B25H, B29R, desB27, desB30 human insulin
B25H, B27G, B28G, B29K, desB30 human insulin
B25H, B27G, B28G, desB30 human insulin
B25H, B27G, desB30 human insulin
B25H, B28G, desB30 human insulin
B25H, B29R, desB30 human insulin
B25H, desB30 human insulin
B27K, desB28, desB29, desB30 human insulin
B26G, desB27, desB28, desB29, desB30 human insulin
B26G, B27K, desB28, desB29, desB30 human insulin
B27G, desB28, desB29, desB30 human insulin
B27G, B28K, desB29, desB30 human insulin
B27G, B28G, desB29, desB30 human insulin
B27G, B28G, B29K, desB30 human insulin
B28E, desB29, desB30 human insulin
B28E, desB30 human insulin
B28H, desB30 human insulin
wherein the insulin analogue further comprises substitutions selected from the group consisting of:
A14D
A14E
A14H
A14P
A14Q
A21G
A14D, A22K
A14D, B16E
A14D, B16H
A14E, A15E
A14E, A21G
A14E, A22K
A14E, B10E
A14E, B16D
A14E, B16E
A14E, B16H
A14E, B22K
A14H, A22K
A14H, B16E
A14H, B16H
A14P, A22K
A14P, B16E
A14P, B16H
A14Q, A22K
A14Q, B16E
A14Q, B16H
A8H, A14E, A22K
A8H, A14E, B10E
A8H, A14E, B10E
A8H, A14E, B10H
A8H, A14E, B22K
A8H, A14H, A22K
A8H, A14H, B16H
A14D, A22K, B16E
A14D, A22K, B16H
A14E, A22K, B16E
A14E, A22K, B16H
A14P, A22K, B16E
A14P, A22K, B16H
A14Q, A22K, B16E
A14Q, A22K, B16H
A14E, B16E, B22K
A14E, B16H, B22K
A14E, B16H, B24H
A14E, A18Q, A21G, B3Q
A14E, desB1, desB2, des3

The following is a non-limiting list of embodiments, which are further described elsewhere herein:

Embodiment 1

An insulin analogue wherein
the A-chain of the insulin analogue comprises at least one mutation relative to the parent insulin, wherein one mutation is in position A14 which is substituted to an amino acid selected from the group consisting of Lys, Glu, Arg, Asp, Pro and His; and
the B-chain of the insulin analogue comprises at least two mutations relative to the parent insulin, wherein two or more mutations are in the form of deletions of the amino acids in positions B27, B28, B29 and B30, or a combination of a deletion of the amino acid in position B30 and a substitution of an amino acid selected from the amino acid substitutions in position: B25 to His, B26 to Gly or Glu, B27 to Gly or Lys and B28 to Asp, His, Gly, Lys or Glu;
wherein, if the mutations in the B-chain of the insulin analogue consist of the combination of a deletion of the amino acid in position B30 and one substitution of the amino acid in position B25 to His, then the at least one mutation in position A14 in the A-chain of the insulin analogue is selected from the group consisting of Lys, Arg and Pro.

Embodiment 2

An insulin analogue according to embodiment 1 which further comprises one or more mutations selected from the group consisting of: A22K, B16D, B16E, B16H, B24H, B25H, B26E, B26G, B27G, B27K, B28D, B28G, B28E, B28H, B28K, B29K, desB26, desB27, desB28 and desB29.

Embodiment 3

An insulin analogue according to embodiment 1, wherein said two or more mutations in the B-chain are in the form of deletions of the amino acids in positions B27, B28, B29 and B30.

Embodiment 4

An insulin analogue according to embodiment 3, which further comprises one or more mutations selected from the group consisting of: A22K, B16D, B16E, B16H, B24H, B25H, B26E, B26G, B27G, B27K, B28D, B28G, B28E, B28H, B28K, B29K and desB26.

Embodiment 5

An insulin analogue according to embodiment 1, wherein said two or more mutations in the B-chain are in the form of a combination of a deletion of the amino acid in position B30 and a substitution of an amino acid in position B25 to His.

Embodiment 6

An insulin analogue according to embodiment 5, which further comprises one or more mutations selected from the group consisting of: A22K, B16D, B16E, B16H, B24H, B26E, B26G, B27G, B27K, B28D, B28G, B28E, B28H, B28K, B29K, desB26, desB27, desB28 and desB29.

Embodiment 7

An insulin analogue according to embodiment 1, wherein said two or more mutations in the B-chain are in the form of a combination of a deletion of the amino acid in position B30 and a substitution of an amino acid in position B26 to Glu or Gly.

Embodiment 8

An insulin analogue according to embodiment 7, which further comprises one or more mutations selected from the group consisting of: A22K, B16D, B16E, B16H, B24H, B25H, B27G, B27K, B28D, B28G, B28E, B28H, B28K, B29K, desB26, desB27, desB28 and desB29.

Embodiment 9

An insulin analogue according to embodiment 1, wherein said two or more mutations in the B-chain are in the form of a combination of a deletion of the amino acid in position B30 and a substitution of an amino acid in position B27 to Gly or Lys.

Embodiment 10

An insulin analogue according to embodiment 9, which further comprises one or more mutations selected from the group consisting of: A22K, B16D, B16E, B16H, B24H, B25H, B26E, B26G, B28D, B28G, B28E, B28H, B28K, B29K, desB26, desB27, desB28 and desB29.

Embodiment 11

An insulin analogue according to embodiment 1, wherein said two or more mutations in the B-chain are in the form of a combination of a deletion of the amino acid in position B30 and a substitution of an amino acid in position B28 to Asp, His, Gly, Lys or Glu.

Embodiment 12

An insulin analogue according to embodiment 11, which further comprises one or more mutations selected from the group consisting of: A22K, B16D, B16E, B16H, B24H, B25H, B26E, B26G, B27G, B27K, B29K, desB26, desB27, desB28 and desB29.

Embodiment 13

An insulin analogue wherein
the A-chain of the insulin analogue comprises at least one mutation relative to the parent insulin, wherein one mutation is in position A14 which is substituted to an amino acid selected from the group consisting of Lys, Glu, Arg, Asp, Pro, Gln and His; and
the B-chain of the insulin analogue comprises at least two mutations relative to the parent insulin, wherein two or more mutations are in the form of deletions of the amino acids in positions B27, B28, B29 and B30, or a combination of a deletion of the amino acid in position B30 and a substitution of an amino acid selected from the amino acid substitutions in position: B24 to Gly or His, B25 to His, B26 to Gly, Glu or Lys, B27 to Gly, Glu or Lys and B28 to Asp, His, Gly, Lys or Glu;
which is selected from the group consisting of:
A8H, A14E, A22K, B16H, B25H, B29R, desB30 human insulin
A8H, A14E, A22K, B25H, B29R, desB30 human insulin
A8H, A14E, B10E, B25H, B26G, B27G, B28G, desB30 human insulin
A8H, A14E, B16H, B25H, desB30 human insulin
A8H, A14E, A22K, B25H, B29R, desB30 human insulin
A8H, A14H, A22K, B16H, B25H, B29R, desB30 human insulin
A8H, A14H, B16H, B25H, desB30 human insulin
A14E, B16H, desB27, desB28, desB29, desB30 human insulin
A14E, B16E, desB27, desB28, desB29, desB30 human insulin
A14E, B16D, desB27, desB28, desB29, desB30 human insulin
A14E, B24G, desB30 human insulin
A14E, B28E, desB29, desB30 human insulin
A14E, B28E, desB30 human insulin
A14E, B28H, desB30 human insulin
A14E, desB1, desB2, desB3, B25H, B27K, desB28, desB29, desB30 human insulin
A14E, desB27, desB28, desB29, desB30 human insulin
A14P, B25H, desB30 human insulin
A21G, desB27, desB30 human insulin
B27K, desB28, desB29, desB30 human insulin
A14D, B25H, desB27, desB28, desB29, desB30 human insulin,
A14E, A15E, B25H, desB30 human insulin
A14E, A18Q, A21G, B3Q, B25H, B27E, desB30 human insulin
A14E, A21G, B25H, desB27, desB30 human insulin
A14E, A21G, B25H, desB30 human insulin
A14E, A22K, B16E, B25H, B29R, desB30 human insulin
A14E, A22K, B16H, B25H, B29R, desB30 human insulin
A14E, A22K, B25H, B26G, B27G, B28G, B29R, desB30 human insulin
A14E, A22K, B25H, B27E, B29R, desB30 human insulin
A14E, B10E, B25H, B26G, B27G, B28G, desB30 human insulin
A14E, B16D, B25H, desB27, desB28, desB29, desB30 human insulin
A14E, B16E, B22K, B25H, B29R, desB30 human insulin
A14E, B16E, B25H, desB27, desB28, desB29, desB30 human insulin
A14E, B16H, B22K, B25H, B29R, desB30 human insulin
A14E, B16H, B25H, desB27, desB28, desB29, desB30 human insulin A14E, B22K, B25H, B26G, B27G, B28G, B29R, desB30 human insulin
A14E, B24G, B25H, desB30 human insulin
A14E, B24G, B25H, desB30 human insulin
A14E, B25H, B26E, B27E, desB30 human insulin
A14E, B25H, B26G, B27E, B28G, desB30 human insulin
A14E, B25H, B26G, B27G B28K, desB29, desB30 human insulin
A14E, B25H, B26G, B27G, desB30 human insulin
A14E, B25H, B26G, B27K, desB28, desB29, desB30 human insulin
A14E, B25H, B26G, B27T, B28G, desB30 human insulin
A14E, B25H, B26G, desB30 human insulin
A14E, B25H, B27G, B28G, desB30 human insulin
A14E, B25H, B27G, desB30 human insulin
A14E, B25H, B28G, desB30 human insulin
A14E, B25H, B29R, desB30 human insulin
A14H, B16H, B24H, B25H, B26G, B27G, B28G, desB30 human insulin
A14H, B16H, B24H, B25H, desB27, desB28, desB29, desB30 human insulin
A14H, B16H, B25H, desB27, desB28, desB29, desB30 human insulin
A14H, B24H, B25H, B26G, B27G, B28G, desB30 human insulin Embodiment 14

An insulin analogue according to embodiment 13, which further comprises one or more mutations selected from the group consisting of: A8H, A18Q, A21A, A21G, A21Q, A22K, B3G, B3A, B3Q, B10E, B10D, B16H, B16E, B16D and B22K.

Embodiment 15

An insulin analogue according to embodiments 13, which further comprises one or more mutations selected from the group consisting of: B16H, B16E and B16D.

Embodiment 16

An insulin analogue according to embodiments 13, which further comprises A22K or B22K.

Embodiment 17

An insulin analogue according to embodiments 13, which further comprises one or more mutations selected from the group consisting of: A21A, A21G, and A21Q.

Embodiment 18

An insulin analogue according to embodiments 13, which further comprises one or more mutations selected from the group consisting of: B3Q, B3G, B3A.

Embodiment 19

An insulin analogue according to embodiments 13, which further comprises A18Q.

Embodiment 20

An insulin analogue according to embodiments 13, which further comprises A8H.

Embodiment 21

An insulin analogue according to embodiments 13, which further comprises one or more mutations selected from the group consisting of: B10E and B10D.

Embodiment 22

An insulin analogue according to embodiments 13, wherein the parent insulin is human insulin.

Embodiment 23

An insulin analogue comprising an A-chain amino acid sequence of formula 1:

Formula (1)(SEQ ID No: 1)
Gly-Ile-Val-Glu-Gln-Cys-Cys-Xaa$_{A8}$-Ser-Ile-Cys-Ser-
Leu-Xaa$_{A14}$-Xaa$_{A15}$-Leu-Glu-Asn-Tyr-Cys-Xaa$_{A21}$-Xaa$_{A22}$ and a B-chain amino acid sequence of formula 2:

Formula (2)(SEQ ID No: 2)
Phe-Val-Xaa$_{B3}$-Gln-His-Leu-Cys-Gly-Ser-Xaa$_{B10}$-Leu-
Val-Glu-Ala-Leu-Xaa$_{B16}$-Leu-Val-Cys-Gly-Glu-Xaa$_{B22}$-
Gly-Xaa$_{B24}$-Xaa$_{B25}$-Xaa$_{B26}$-Xaa$_{B27}$-Xaa$_{B28}$-Xaa$_{B29}$ wherein
  Xaa$_{A8}$ is independently selected from Thr and His;
  Xaa$_{A14}$ is independently selected from Asp, His, Lys, Arg, Pro, Gln and Glu;
  Xaa$_{A15}$ is independently selected from Gln and Glu;
  Xaa$_{A21}$ is independently selected from Asn, Gln, Gly and Ala;
  Xaa$_{A22}$ is absent or Lys;
  Xaa$_{B3}$ is independently selected from Asn, Gln, Gly and Ala;
  Xaa$_{B10}$ is independently selected from His, Glu and Asp;
  Xaa$_{B16}$ is independently selected from Tyr, Asp, His and Glu;
  Xaa$_{B22}$ is absent or independently selected from Arg and Lys;
  Xaa$_{B24}$ is absent or independently selected from Phe, Gly and His;
  Xaa$_{B25}$ is absent or independently selected from Phe, Asn, Ala and His;
  Xaa$_{B26}$ is absent or independently selected from Tyr, Gly, Lys and Glu;
  Xaa$_{B27}$ is absent or independently selected from Gly, Lys and Thr;
  Xaa$_{B28}$ is absent or independently selected from Pro, Gly, His, Lys, Asp and Glu;
  Xaa$_{B29}$ is absent or Lys;
  the C-terminal may optionally be derivatized as an amide;
  wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge;
  wherein the A-chain of the insulin analogue comprises at least one mutation relative to the parent insulin and the B-chain of the insulin analogue comprises at least two mutations relative to the parent insulin; and wherein, if the mutations in the B-chain of the insulin analogue consist of the combination of a deletion of the amino acid in position B30 and a substitution of the amino acid in position B25 to His, then the at least one mutation in position A14 in the A-chain of the insulin analogue is selected from the group consisting of Lys, Arg and Pro.

Embodiment 24

An insulin analogue comprising an A-chain amino acid sequence of formula 3:

```
                                Formula (3)(SEQ ID No: 3)
Gly-Ile-Val-Glu-Gln-Cys-Cys-Thr-Ser-Ile-Cys-Ser- Leu-Xaa_{A14}-Xaa_{A15}-Leu-Glu-Asn-Tyr-Cys-Xaa_{A21}-Xaa_{A22}
``` and a B-chain amino acid sequence of formula 4:

```
                                Formula (4)(SEQ ID No: 4)
Phe-Val-Xaa_{B3}-Gln-His-Leu-Cys-Gly-Ser-His-Leu-Val- Glu-Ala-Leu-Xaa_{B16}-Leu-Val-Cys-Gly-Glu-Xaa_{B22}-

Gly-Xaa_{B24}-Xaa_{B25}-Xaa_{B26}-Xaa_{B27}-Xaa_{B28}-Xaa_{B29}
``` wherein $Xaa_{A14}$ is independently selected from Asp, His, Lys, Arg, Pro, Gln and Glu;

$Xaa_{A15}$ is independently selected from Gln and Glu;

$Xaa_{A21}$ is independently selected from Asn, Gln, Gly and Ala;

$Xaa_{A22}$ is absent or Lys;

$Xaa_{B3}$ is independently selected from Asn, Gln, Gly and Ala;

$Xaa_{B16}$ is independently selected from Tyr, Asp, His and Glu;

$Xaa_{B22}$ is absent or independently selected from Arg and Lys;

$Xaa_{B24}$ is absent or independently selected from Phe, Gly and His;

$Xaa_{B25}$ is absent or independently selected from Phe, Asn, Ala and His;

$Xaa_{B26}$ is absent or independently selected from Tyr, Gly, Lys and Glu;

$Xaa_{B27}$ is absent or independently selected from Gly, Lys and Thr;

$Xaa_{B28}$ is absent or independently selected from Pro, Gly, His, Lys, Asp and Glu;

$Xaa_{B29}$ is absent or Lys;

the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge; wherein the A-chain of the insulin analogue comprises at least one mutation relative to the parent insulin and the B-chain of the insulin analogue comprises at least two mutations relative to the parent insulin; and wherein, if the mutations in the B-chain of the insulin analogue consist of the combination of a deletion of the amino acid in position B30 and a substitution of the amino acid in position B25 to His, then the at least one mutation in position A14 in the A-chain of the insulin analogue is selected from the group consisting of Lys, Arg and Pro.

Embodiment 25

An insulin analogue comprising an A-chain amino acid sequence of formula 5:

```
                                Formula (5)(SEQ ID No: 5)
Gly-Ile-Val-Glu-Gln-Cys-Cys-Thr-Ser-Ile-Cys-Ser- Leu-Xaa_{A14}-Gln-Leu-Glu-Asn-Tyr-Cys-Xaa_{A21}-Xaa_{A22}
``` and a B-chain amino acid sequence of formula 6:

```
                                Formula (2)(SEQ ID No: 6)
Phe-Val-Xaa_{B3}-Gln-His-Leu-Cys-Gly-Ser-His-Leu-Val- Glu-Ala-Leu-Xaa_{B16}-Leu-Val-Cys-Gly-Glu-Arg-Gly- Xaa_{B24}-Xaa_{B25}-Xaa_{B26}-Xaa_{B27}-Xaa_{B28}-Xaa_{B29}
``` wherein $Xaa_{A14}$ is independently selected from Asp, His, Lys, Arg, Pro, Gln and Glu;

$Xaa_{A21}$ is independently selected from Asn, Gln, Gly and Ala;

$Xaa_{A22}$ is absent or Lys;

$Xaa_{B3}$ is independently selected from Asn, Gln, Gly and Ala;

$Xaa_{B16}$ is independently selected from Tyr, Asp, His and Glu;

$Xaa_{B24}$ is absent or independently selected from Phe, Gly and His;

$Xaa_{B25}$ is absent or independently selected from Phe, Asn, Ala and His;

$Xaa_{B26}$ is absent or independently selected from Tyr, Gly, Lys and Glu;

$Xaa_{B27}$ is absent or independently selected from Gly, Lys and Thr;

$Xaa_{B28}$ is absent or independently selected from Pro, Gly, His, Lys, Asp and Glu;

$Xaa_{B29}$ is absent or Lys;

the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge;

wherein the A-chain of the insulin analogue comprises at least one mutation relative to the parent insulin and the B-chain of the insulin analogue comprises at least two mutations relative to the parent insulin; and wherein, if the mutations in the B-chain of the insulin analogue consist of the combination of a deletion of the amino acid in position B30 and a substitution of the amino acid in position B25 to His, then the at least one mutation in position A14 in the A-chain of the insulin analogue is selected from the group consisting of Lys, Arg and Pro.

Embodiment 26

An insulin analogue comprising an A-chain amino acid sequence of formula 7:

Formula (7) (SEQ ID No: 7)
Gly-Ile-Val-Glu-Gln-Cys-Cys-Thr-Ser-Ile-Cys-Ser-

Leu-Xaa$_{A14}$-Gln-Leu-Glu-Asn-Tyr-Cys-Asn-Xaa$_{A22}$ and a B-chain amino acid sequence of formula 8:

Formula (8) (SEQ ID No: 8)
Phe-Val-Asn-Gln-His-Leu-Cys-Gly-Ser-His-Leu-Val-

Glu-Ala-Leu-Xaa$_{B16}$-Leu-Val-Cys-Gly-Glu-Arg-Gly-

Xaa$_{B24}$-Xaa$_{B25}$-Xaa$_{B26}$-Xaa$_{B27}$-Xaa$_{B28}$-Xaa$_{B29}$ wherein

Xaa$_{A14}$ is independently selected from Asp, His, Lys, Arg, Pro and Glu;

Xaa$_{A22}$ is absent or Lys;

Xaa$_{B16}$ is independently selected from Tyr, Asp, His and Glu;

Xaa$_{B24}$ is independently selected from Phe and His;

Xaa$_{B25}$ is independently selected from Phe and His;

Xaa$_{B26}$ is independently selected from Tyr, Gly and Glu;

Xaa$_{B27}$ is absent or independently selected from Gly, Lys and Thr;

Xaa$_{B28}$ is absent or independently selected from Pro, Gly, His, Lys, Asp and Glu;

Xaa$_{B29}$ is absent or Lys;

the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge;

wherein the A-chain of the insulin analogue comprises at least one mutation relative to the parent insulin and the B-chain of the insulin analogue comprises at least two mutations relative to the parent insulin; and wherein, if the mutations in the B-chain of the insulin analogue consist of the combination of a deletion of the amino acid in position B30 and a substitution of the amino acid in position B25 to His, then the at least one mutation in position A14 in the A-chain of the insulin analogue is selected from the group consisting of Lys, Arg and Pro.

Embodiment 27

An insulin analogue comprising an A-chain amino acid sequence of formula 9:

Formula (9) (SEQ ID No: 9)
Gly-Ile-Val-Glu-Gln-Cys-Cys-Thr-Ser-Ile-Cys-Ser-

Leu-Xaa$_{A14}$-Gln-Leu-Glu-Asn-Tyr-Cys-Asn and a B-chain amino acid sequence of formula 10:

Formula (10) (SEQ ID No: 10)
Phe-Val-Asn-Gln-His-Leu-Cys-Gly-Ser-His-Leu-Val-

Glu-Ala-Leu-Tyr-Leu-Val-Cys-Gly-Glu-Arg-Gly-

Xaa$_{B24}$-Xaa$_{B25}$-Xaa$_{B26}$-Xaa$_{B27}$-Xaa$_{B28}$-Xaa$_{B29}$ wherein

Xaa$_{A14}$ is independently selected from Asp, His, Lys, Arg, Pro, Glu and Gln;

Xaa$_{B24}$ is independently selected from Phe, Gly and His;

Xaa$_{B25}$ is independently selected from Phe and His;

Xaa$_{B26}$ is independently selected from Tyr, Gly, Glu and Lys;

Xaa$_{B27}$ is absent or independently selected from Gly, Lys and Thr;

Xaa$_{B28}$ is absent or independently selected from Pro, Gly, His, Lys, Asp and Glu;

Xaa$_{B29}$ is absent or Lys;

the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge;

wherein the A-chain of the insulin analogue comprises at least one mutation relative to the parent insulin and the B-chain of the insulin analogue comprises at least two mutations relative to the parent insulin; and wherein, if the mutations in the B-chain of the insulin analogue consist of the combination of a deletion of the amino acid in position B30 and a substitution of the amino acid in position B25 to His, then the at least one mutation in position A14 in the A-chain of the insulin analogue is selected from the group consisting of Lys, Arg and Pro.

Embodiment 28

An insulin analogue wherein
  the A-chain of the insulin analogue comprises at least one mutation relative to the parent insulin, wherein one mutation is in position A14 which is substituted to an amino acid selected from the group consisting of Lys, Glu, Arg, Asp, Pro, Gln and His; and
  the B-chain of the insulin analogue comprises at least two mutations relative to the parent insulin, wherein two or more mutations are in the form of deletions of the amino acids in positions B27, B28, B29 and B30, or a combination of a deletion of the amino acid in position B30 and a substitution of an amino acid selected from the amino acid substitutions in position: B24 to Gly or His, B25 to His, B26 to Gly, B27 to Gly, His, Thr or Lys and B28 to His, Gly, Lys or Glu;
which is selected from the group consisting of:
  B25H, desB26, desB27, desB28, desB29, desB30 human insulin
  B25H, desB27, desB28, desB29, desB30 human insulin
  B25H, B27K, desB28, desB29, desB30 human insulin
  B25H, B26G, desB27, desB28, desB29, desB30 human insulin
  B25H, B26G, B27K, desB28, desB29, desB30 human insulin B25H, B26G, B27G, desB28, desB29, desB30 human insulin
B25H, B26G, B27G, B28K, desB29, desB30 human insulin
B25H, B26G, B27G, B28G, desB29, desB30 human insulin
B25H, B26G, B27G, B28G, B29K, desB30 human insulin
B25H, B27G, desB28, desB29, desB30 human insulin
B25H, B27G, B28K, desB29, desB30 human insulin
B25H, B27G, B28G, desB29, desB30 human insulin
B25H, B27G, B28G, B29K, desB30 human insulin
B27K, desB28, desB29, desB30 human insulin
B26G, desB27, desB28, desB29, desB30 human insulin
B26G, B27K, desB28, desB29, desB30 human insulin
B27G, desB28, desB29, desB30 human insulin
B27G, B28K, desB29, desB30 human insulin
B27G, B28G, desB29, desB30 human insulin, and
B27G, B28G, B29K, desB30 human insulin wherein the insulin analogue furthermore comprises substitutions selected from the group consisting of:
A14E
A14D
A14H
A14E, A22K
A14D, A22K
A14H, A22K
A14D, B16H
A14E, B16H
A14H, B16H
A14E, A22K, B16H
A14H, A22K, B16H, and
A14D, A22K, B16H Embodiment 29

An insulin analogue wherein
the A-chain of the insulin analogue comprises at least one mutation relative to the parent insulin, wherein one mutation is in position A14 which is substituted to an amino acid selected from the group consisting of Lys, Glu, Arg, Asp, Pro, Gln and His; and
the B-chain of the insulin analogue comprises at least two mutations relative to the parent insulin, wherein two or more mutations are in the form of deletions of the amino acids in positions B27, B28, B29 and B30, or a combination of a deletion of the amino acid in position B30 and a substitution of an amino acid selected from the amino acid substitutions in position: B24 to Gly or His, B25 to His, B26 to Gly, B27 to Gly, His, Thr or Lys and B28 to His, Gly, Lys or Glu;

which is selected from the group consisting of:
desB27, desB28, desB29, desB30 human insulin
desB27, desB30 human insulin
desB28, desB29, desB30 human insulin
B24H, B25H, desB27, desB28, desB29, desB30 human insulin
B24H, B25H, B26G, B27G, B28G, desB30 human insulin
B24G, B25H, desB30 human insulin
B24G, desB30 human insulin
B25H, desB26, desB27, desB28, desB29, desB30 human insulin
B25H, desB27, desB28, desB29, desB30 human insulin
B25H, desB27, desB30 human insulin
B25H, B27K, desB28, desB29, desB30 human insulin
B25H, B26E, B27E, desB30 human insulin
B25H, B26G, desB27, desB28, desB29, desB30 human insulin
B25H, B26G, B27K, desB28, desB29, desB30 human insulin
B25H, B26G, B27G, desB28, desB29, desB30 human insulin
B25H, B26G, B27G, B28K, desB29, desB30 human insulin
B25H, B26G, B27G, B28G, desB29, desB30 human insulin
B25H, B26G, B27G, B28G, B29K, desB30 human insulin
B25H, B26G, B27E, B28G, desB30 human insulin
B25H, B26G, B27T, B28G, desB30 human insulin
B25H, B26G, B27G, B28G, B29R, desB30 human insulin
B25H, B26G, B27G, B28G, desB30 human insulin
B25H, B26G, B27G, desB30 human insulin
B25H, B26G, desB30 human insulin
B25H, B27E, B29R, desB30 human insulin
B25H, B27E, B29R, desB30 human insulin
B25H, B27E, desB30 human insulin
B25H, B27G, desB28, desB29, desB30 human insulin
B25H, B27K, desB28, desB29, desB30 human insulin
B25H, B27G, B28K, desB29, desB30 human insulin
B25H, B27G, B28G, desB29, desB30 human insulin
B25H, B29R, desB27, desB30 human insulin
B25H, B27G, B28G, B29K, desB30 human insulin
B25H, B27G, B28G, desB30 human insulin
B25H, B27G, desB30 human insulin
B25H, B28G, desB30 human insulin
B25H, B29R, desB30 human insulin
B25H, desB30 human insulin
B27K, desB28, desB29, desB30 human insulin
B26G, desB27, desB28, desB29, desB30 human insulin
B26G, B27K, desB28, desB29, desB30 human insulin
B27G, desB28, desB29, desB30 human insulin
B27G, B28K, desB29, desB30 human insulin
B27G, B28G, desB29, desB30 human insulin
B27G, B28G, B29K, desB30 human insulin
B28E, desB29, desB30 human insulin
B28E, desB30 human insulin
B28H, desB30 human insulin wherein the insulin analogue further comprises substitutions selected from the group consisting of:
A14D
A14E
A14H
A14P
A14Q
A14D, A22K
A14D, B16E
A14D, B16H
A14E, A15E
A14E, A21G
A14E, A22K
A14E, B10E
A14E, B16D
A14E, B16E
A14E, B16H
A14E, B22K
A14H, A22K
A14H, B16E
A14H, B16H
A14P, A22K
A14P, B16E
A14P, B16H
A14Q, A22K
A14Q, B16E
A14Q, B16H
A8H, A14E, A22K A8H, A14E, B10E
A8H, A14E, B10E
A8H, A14E, B10H
A8H, A14E, B22K
A8H, A14H, A22K
A8H, A14H, B16H
A14D, A22K, B16E
A14D, A22K, B16H
A14E, A22K, B16E
A14E, A22K, B16H
A14P, A22K, B16E
A14P, A22K, B16H
A14Q, A22K, B16E
A14Q, A22K, B16H
A14E, B16E, B22K
A14E, B16H, B22K
A14E, B16H, B24H
A14E, A18Q, A21G, B3Q
A14E, desB1, desB2, des3

Embodiment 30

An insulin analogue wherein
the A-chain of the insulin analogue comprises at least one mutation relative to the parent insulin, wherein one mutation is in position A14 which is substituted to an amino acid selected from the group consisting of Lys, Glu, Arg, Asp, Pro, Gln and His; and
the B-chain of the insulin analogue comprises at least two mutations relative to the parent insulin, wherein two or more mutations are in the form of deletions of the amino acids in positions B27, B28, B29 and B30, or a combination of a deletion of the amino acid in position B30 and a substitution of an amino acid selected from the amino acid substitutions in position: B24 to Gly or His, B25 to His, B26 to Gly, B27 to Gly, His, Thr or Lys and B28 to His, Gly, Lys or Glu;
which is selected from the group consisting of:
desB27, desB28, desB29, desB30 human insulin
desB27, desB30 human insulin
desB28, desB29, desB30 human insulin
B24H, B25H, desB27, desB28, desB29, desB30 human insulin
B24H, B25H, B26G, B27G, B28G, desB30 human insulin
B24G, B25H, desB30 human insulin
B24G, desB30 human insulin
B25H, desB27, desB28, desB29, desB30 human insulin
B25H, desB27, desB30 human insulin
B25H, B26E, B27E, desB30 human insulin
B25H, B26G, B27K, desB28, desB29, desB30 human insulin
B25H, B26G, B27G, B28K, desB29, desB30 human insulin
B25H, B26G, B27E, B28G, desB30 human insulin
B25H, B26G, B27T, B28G, desB30 human insulin
B25H, B26G, B27G, B28G, B29R, desB30 human insulin
B25H, B26G, B27G, B28G, desB30 human insulin
B25H, B26G, B27G, desB30 human insulin
B25H, B26G, desB30 human insulin
B25H, B27E, B29R, desB30 human insulin
B25H, B27E, B29R, desB30 human insulin
B25H, B27E, desB30 human insulin
B25H, B27K, desB28, desB29, desB30 human insulin
B25H, B27G, B28G, desB30 human insulin
B25H, B27G, desB30 human insulin
B25H, B28G, desB30 human insulin
B25H, B29R, desB30 human insulin
B25H, desB30 human insulin
B28E, desB29, desB30 human insulin
B28E, desB30 human insulin
B28H, desB30 human insulin
wherein the insulin analogue further comprises substitutions selected from the group consisting of:
A14D
A14E
A14P
A14E, A15E
A14E, A21G
A14E, A22K
A14E, B10E
A14E, B16D
A14E, B16E
A14E, B16H
A14E, B22K
A14H, B16H
A8H, A14E, A22K
A8H, A14E, B10E
A8H, A14E, B10E
A8H, A14E, B10H
A8H, A14E, B22K
A8H, A14H, A22K
A8H, A14H, B16H
A14E, A22K, B16E
A14E, A22K, B16H
A14E, B16E, B22K
A14E, B16H, B22K
A14E, B16H, B24H
A14E, A18Q, A21G, B3Q
A14E, desB1, desB2, des3

Embodiment 31

An insulin analogue according to any of the embodiments 28-30, wherein the insulin analogue is not:
A14E, B25H, desB30 human insulin
A14H, B25H, desB30 human insulin
A14E, B16E, B25H, desB30 human insulin
A14E, B16H, B25H, desB30 human insulin
A14E, B25H, desB26, desB27, desB28, desB29, desB30 human insulin
A14E, B25H, desB27, desB28, desB29, desB30 human insulin
A14E, B25H, B27K, desB28, desB29, desB30 human insulin
A14E, B25H, B26G, desB27, desB28, desB29, desB30 human insulin
A14E, B27G, B28K, desB29, desB30 human insulin, or
A14E, B27G, B28G, desB29, desB30 human insulin Embodiment 32

An insulin analogue according to embodiment 29, which is selected from the group consisting of:
A14D, B25H, desB27, desB28, desB29, desB30 human insulin
A14E, A22K, B25H, desB27, desB28, desB29, desB30 human insulin
A14E, B16D, B25H, desB27, desB28, desB29, desB30 human insulin
A14E, B16E, B25H, desB27, desB28, desB29, desB30 human insulin
A14E, B16H, B25H, desB27, desB28, desB29, desB30 human insulin
A14E, desB27, desB28, desB29, desB30 human insulin A14E, B16D, desB27, desB28, desB29, desB30 human insulin
A14E, B16E, desB27, desB28, desB29, desB30 human insulin
A14E, B16H, desB27, desB28, desB29, desB30 human insulin
A14H, B16H, B25H, desB27, desB28, desB29, desB30 human insulin
A14H, B16H, B24H, B25H, desB27, desB28, desB29, desB30 human insulin
A14E, B28E, desB30 human insulin
A14E, B28H, desB30 human insulin
A14E, B28E, desB29, desB30 human insulin
A14P, B25H, desB30 human insulin
A14K, B25H, desB30 human insulin
A14H, B24H, B25H, B26G, B27G, B28G, desB30 human insulin
A14H, B16H, B24H, B25H, B26G, B27G, B28G, desB30 human insulin Embodiment 33

An insulin analogue according to embodiment 29, which is selected from the group consisting of:
A8H, A14E, A22K, B16H, B25H, B29R, desB30 human insulin
A8H, A14E, A22K, B25H, B29R, desB30 human insulin
A8H, A14E, B10E, B25H, B26G, B27G, B28G, desB30 human insulin
A8H, A14E, B16H, B25H, desB30 human insulin
A8H, A14E, B22K, B25H, B29R, desB30 human insulin
A8H, A14H, A22K, B16H, B25H, B29R, desB30 human insulin
A8H, A14H, B16H, B25H, desB30 human insulin
A14D, B25H, desB27, desB28, desB29, desB30 human insulin,
A14E, A15E, B25H, desB30 human insulin
A14E, A18Q, A21G, B3Q, B25H, B27E, desB30 human insulin
A14E, A21G, B25H, desB27, desB30 human insulin
A14E, A21G, B25H, desB30 human insulin
A14E, A22K, B16E, B25H, B29R, desB30 human insulin
A14E, A22K, B16H, B25H, B29R, desB30 human insulin
A14E, A22K, B25H, B26G, B27G, B28G, B29R, desB30 human insulin
A14E, A22K, B25H, B27E, B29R, desB30 human insulin
A14E, B10E, B25H, B26G, B27G, B28G, desB30 human insulin
A14E, B16D, B25H, desB27, desB28, desB29, desB30 human insulin
A14E, B16D, desB27, desB28, desB29, desB30 human insulin
A14E, B16E, B22K, B25H, B29R, desB30 human insulin
A14E, B16E, B25H, desB27, desB28, desB29, desB30 human insulin
A14E, B16E, desB27, desB28, desB29, desB30 human insulin
A14E, B16H, B22K, B25H, B29R, desB30 human insulin
A14E, B16H, B25H, desB27, desB28, desB29, desB30 human insulin
A14E, B16H, desB27, desB28, desB29, desB30 human insulin
A14E, B22K, B25H, B26G, B27G, B28G, B29R, desB30 human insulin
A14E, B24G, B25H, desB30 human insulin
A14E, B24G, B25H, desB30 human insulin
A14E, B24G, desB30 human insulin
A14E, B25H, B26E, B27E, desB30 human insulin
A14E, B25H, B26G, B27E, B28G, desB30 human insulin
A14E, B25H, B26G, B27G B28K, desB29, desB30 human insulin
A14E, B25H, B26G, B27G, desB30 human insulin
A14E, B25H, B26G, B27K, desB28, desB29, desB30 human insulin
A14E, B25H, B26G, B27T, B28G, desB30 human insulin
A14E, B25H, B26G, desB30 human insulin
A14E, B25H, B27G, B28G, desB30 human insulin
A14E, B25H, B27G, desB30 human insulin
A14E, B25H, B28G, desB30 human insulin
A14E, B25H, B29R, desB30 human insulin
A14E, B28E, desB29, desB30 human insulin
A14E, B28E, desB30 human insulin
A14E, B28H, desB30 human insulin
A14E, desB1, desB2, desB3, B25H, B27K, desB28, desB29, desB30 human insulin
A14E, desB27, desB28, desB29, desB30 human insulin
A14H, B16H, B24H, B25H, B26G, B27G, B28G, desB30 human insulin
A14H, B16H, B24H, B25H, desB27, desB28, desB29, desB30 human insulin
A14H, B16H, B25H, desB27, desB28, desB29, desB30 human insulin
A14H, B24H, B25H, B26G, B27G, B28G, desB30 human insulin
A14P, B25H, desB30 human insulin
A21G, desB27, desB30 human insulin
B27K, desB28, desB29, desB30 human insulin Embodiment 34

An insulin analogue according to embodiment 29, which is selected from the group consisting of:
A14E, A22K, B16H, B25H, B29R, desB30 human insulin
A14E, A22K, B16E, B25H, B29R, desB30 human insulin
A14E, A22K, B16H, B25H, desB27, B29R, desB30 human insulin
A14E, A22K, B16E, B25H, desB27, B29R, desB30 human insulin
A14E, A22K, B25H, B27E, B29R, desB30 human insulin
A14E, A22K, B16H, B25H, B27E, B29R, desB30 human insulin
A14E, A22K, B16E, B25H, B27E, B29R, desB30 human insulin
A14E, A22K, B25H, B26G, B27G, B28G, B29R, desB30 human insulin
A14E, A22K, B16H, B25H, B26G, B27G, B28G, B29R, desB30 human insulin
A14E, A22K, B16E, B25H, B26G, B27G, B28G, B29R, desB30 human insulin
A14E, A22K, B16E, B25H, B26G, B27E, B28G, B29R, desB30 human insulin
A14E, A22K, B16H, B25H, B26G, B27E, B28G, B29R, desB30 human insulin
A14E, A22K, B16H, B25H, desB30 human insulin
A14E, A22K, B16E, B25H, desB30 human insulin
A14E, A22K, B25H, B27E, desB30 human insulin
A14E, A22K, B16H, B25H, B27E, desB30 human insulin
A14E, A22K, B16E, B25H, B27E, desB30 human insulin
A14E, A22K, B25H, B26G, B27G, B28G, desB30 human insulin
A14E, A22K, B16H, B25H, B26G, B27G, B28G, desB30 human insulin
A14E, A22K, B16E, B25H, B26G, B27G, B28G, desB30 human insulin A14E, A22K, B16E, B25H, B26G, B27E, B28G, desB30 human insulin
A14E, A22K, B16H, B25H, B26G, B27E, B28G, desB30 human insulin
A14E, A22K, B16H, B25H, desB27, desB30 human insulin
A14E, A22K, B16E, B25H, desB27, desB30 human insulin
A14Q, A22K, B16H, B25H, B29R, desB30 human insulin
A14Q, A22K, B16E, B25H, B29R, desB30 human insulin
A14Q, A22K, B16H, B25H, desB27, B29R, desB30 human insulin
A14Q, A22K, B16E, B25H, desB27, B29R, desB30 human insulin
A14Q, A22K, B25H, B27E, B29R, desB30 human insulin
A14Q, A22K, B16H, B25H, B27E, B29R, desB30 human insulin
A14Q, A22K, B16E, B25H, B27E, B29R, desB30 human insulin
A14Q, A22K, B25H, B26G, B27G, B28G, B29R, desB30 human insulin
A14Q, A22K, B16H, B25H, B26G, B27G, B28G, B29R, desB30 human insulin
A14Q, A22K, B16E, B25H, B26G, B27G, B28G, B29R, desB30 human insulin
A14Q, A22K, B16E, B25H, B26G, B27E, B28G, B29R, desB30 human insulin
A14Q, A22K, B16H, B25H, B26G, B27E, B28G, B29R, desB30 human insulin
A14Q, A22K, B16H, B25H, desB30 human insulin
A14Q, A22K, B16E, B25H, desB30 human insulin
A14Q, A22K, B25H, B27E, desB30 human insulin
A14Q, A22K, B16H, B25H, B27E, desB30 human insulin
A14Q, A22K, B16E, B25H, B27E, desB30 human insulin
A14Q, A22K, B25H, B26G, B27G, B28G, desB30 human insulin
A14Q, A22K, B16H, B25H, B26G, B27G, B28G, desB30 human insulin
A14Q, A22K, B16E, B25H, B26G, B27G, B28G, desB30 human insulin
A14Q, A22K, B16E, B25H, B26G, B27E, B28G, desB30 human insulin
A14Q, A22K, B16H, B25H, B26G, B27E, B28G, desB30 human insulin
A14Q, A22K, B16H, B25H, desB27, desB30 human insulin
A14Q, A22K, B16E, B25H, desB27, desB30 human insulin
A14P, A22K, B16H, B25H, B29R, desB30 human insulin
A14P, A22K, B16E, B25H, B29R, desB30 human insulin
A14P, A22K, B16H, B25H, desB27, B29R, desB30 human insulin
A14P, A22K, B16E, B25H, desB27, B29R, desB30 human insulin
A14P, A22K, B25H, B27E, B29R, desB30 human insulin
A14P, A22K, B16H, B25H, B27E, B29R, desB30 human insulin
A14P, A22K, B16E, B25H, B27E, B29R, desB30 human insulin
A14P, A22K, B25H, B26G, B27G, B28G, B29R, desB30 human insulin
A14P, A22K, B16H, B25H, B26G, B27G, B28G, B29R, desB30 human insulin
A14P, A22K, B16E, B25H, B26G, B27G, B28G, B29R, desB30 human insulin
A14P, A22K, B16E, B25H, B26G, B27E, B28G, B29R, desB30 human insulin
A14P, A22K, B16H, B25H, B26G, B27E, B28G, B29R, desB30 human insulin
A14P, A22K, B16H, B25H, desB30 human insulin
A14P, A22K, B16E, B25H, desB30 human insulin
A14P, A22K, B25H, B27E, desB30 human insulin
A14P, A22K, B16H, B25H, B27E, desB30 human insulin
A14P, A22K, B16E, B25H, B27E, desB30 human insulin
A14P, A22K, B25H, B26G, B27G, B28G, desB30 human insulin
A14P, A22K, B16H, B25H, B26G, B27G, B28G, desB30 human insulin
A14P, A22K, B16E, B25H, B26G, B27G, B28G, desB30 human insulin
A14P, A22K, B16E, B25H, B26G, B27E, B28G, desB30 human insulin
A14P, A22K, B16H, B25H, B26G, B27E, B28G, desB30 human insulin
A14P, A22K, B16H, B25H, desB27, desB30 human insulin
A14P, A22K, B16E, B25H, desB27, desB30 human insulin
A14D, A22K, B16H, B25H, B29R, desB30 human insulin
A14D, A22K, B16E, B25H, B29R, desB30 human insulin
A14D, A22K, B16H, B25H, desB27, B29R, desB30 human insulin
A14D, A22K, B16E, B25H, desB27, B29R, desB30 human insulin
A14D, A22K, B25H, B27E, B29R, desB30 human insulin
A14D, A22K, B16H, B25H, B27E, B29R, desB30 human insulin
A14D, A22K, B16E, B25H, B27E, B29R, desB30 human insulin
A14D, A22K, B25H, B26G, B27G, B28G, B29R, desB30 human insulin
A14D, A22K, B16H, B25H, B26G, B27G, B28G, B29R, desB30 human insulin
A14D, A22K, B16E, B25H, B26G, B27G, B28G, B29R, desB30 human insulin
A14D, A22K, B16E, B25H, B26G, B27E, B28G, B29R, desB30 human insulin
A14D, A22K, B16H, B25H, B26G, B27E, B28G, B29R, desB30 human insulin
A14D, A22K, B16H, B25H, desB30 human insulin
A14D, A22K, B16E, B25H, desB30 human insulin
A14D, A22K, B25H, B27E, desB30 human insulin
A14D, A22K, B16H, B25H, B27E, desB30 human insulin
A14D, A22K, B16E, B25H, B27E, desB30 human insulin
A14D, A22K, B25H, B26G, B27G, B28G, desB30 human insulin
A14D, A22K, B16H, B25H, B26G, B27G, B28G, desB30 human insulin
A14D, A22K, B16E, B25H, B26G, B27G, B28G, desB30 human insulin
A14D, A22K, B16E, B25H, B26G, B27E, B28G, desB30 human insulin
A14D, A22K, B16H, B25H, B26G, B27E, B28G, desB30 human insulin
A14D, A22K, B16H, B25H, desB27, desB30 human insulin
A14D, A22K, B16E, B25H, desB27, desB30 human insulin Embodiment 35

An insulin analogue according to embodiment 29, which is selected from the group consisting of:
A14E, A22K, B16H, B25H, desB27, B29R, desB30 human insulin
A14E, A22K, B16E, B25H, desB27, B29R, desB30 human insulin
A14E, A22K, B16H, B25H, desB27, desB30 human insulin
A14E, A22K, B16E, B25H, desB27, desB30 human insulin
A14E, B16H, B25H, desB27, desB30 human insulin
A14E, B16E, B25H, desB27, desB30 human insulin A14P, A22K, B16H, B25H, desB27, B29R, desB30 human insulin
A14P, A22K, B16E, B25H, desB27, B29R, desB30 human insulin
A14P, A22K, B16H, B25H, desB27, desB30 human insulin
A14P, A22K, B16E, B25H, desB27, desB30 human insulin
A14P, B16H, B25H, desB27, desB30 human insulin
A14P, B16E, B25H, desB27, desB30 human insulin
A14D, A22K, B16H, B25H, desB27, B29R, desB30 human insulin
A14D, A22K, B16E, B25H, desB27, B29R, desB30 human insulin
A14D, A22K, B16H, B25H, desB27, desB30 human insulin
A14D, A22K, B16E, B25H, desB27, desB30 human insulin
A14D, B16H, B25H, desB27, desB30 human insulin
A14D, B16E, B25H, desB27, desB30 human insulin
A14Q, A22K, B16H, B25H, desB27, B29R, desB30 human insulin
A14Q, A22K, B16E, B25H, desB27, B29R, desB30 human insulin
A14Q, A22K, B16H, B25H, desB27, desB30 human insulin
A14Q, A22K, B16E, B25H, desB27, desB30 human insulin
A14Q, B16H, B25H, desB27, desB30 human insulin
A14Q, B16E, B25H, desB27, desB30 human insulin Embodiment 36

A pharmaceutical composition comprising a biologically active amount of the insulin analogue according to any of the embodiments 1-35 and a pharmaceutically acceptable carrier.

Embodiment 37

A pharmaceutical composition comprising two or more insulin analogues according to any of the embodiments 1-35 wherein each analogue is defined by having at least one mutation, which is absent or different in any of the other variants.

Embodiment 38

A pharmaceutical composition according to any of the embodiments 36-37 which further comprises a pharmaceutical acceptable carrier and/or excipient, and optionally an adjuvant.

Embodiment 39

A method for the treatment of diabetes mellitus in a subject comprising administering to a subject an insulin analogue according to any of the embodiments 1-35 or a pharmaceutical composition according to any of the embodiments 36-37.

Embodiment 40

A method of reducing the blood glucose level in mammals by administrating to a patient in need of such treatment a therapeutically active dose of an insulin analogue according to any of the embodiments 1-35 or a pharmaceutical composition according to any of the embodiments 36-37.

Embodiment 41

Method according to embodiment 39 or 40 being an oral administration.

Embodiment 42

Method according to embodiment 39 or 40 being parenteral administration.

Embodiment 43

Method according to embodiment 39 or 40 being intratracheal administration.

Embodiment 44

An insulin analogue according to any of the embodiments 1-35 for use as a medicament for the treatment or prevention of hyperglycemia including stress induced hyperglycemia, type 2 diabetes, impaired glucose tolerance, type 1 diabetes, and burns, operation wounds and other diseases or injuries where an anabolic effect is needed in the treatment, myocardial infarction, stroke, coronary heart disease and other cardiovascular disorders and treatment of critically ill diabetic and non-diabetic patients.

Embodiment 45

Insulin analogue according to any of the embodiments 1-35 for use as a medicament for delaying or preventing disease progression in type 2 diabetes.

Embodiment 46

An insulin analogue according to any of the embodiments 1-35 for use as a medicament for the treatment or prevention of hyperglycemia including stress induced hyperglycemia, type 2 diabetes, impaired glucose tolerance, type 1 diabetes, and burns, operation wounds and other diseases or injuries where an anabolic effect is needed in the treatment, myocardial infarction, stroke, coronary heart disease and other cardiovascular disorders is provided.

Embodiment 47

A nucleic acid sequence encoding an insulin analogue according to any of the embodiments 1-35, a derivative thereof, a partial sequence thereof, a degenerated sequence thereof or a sequence which hybridizes thereto under stringent conditions.

Embodiment 48

A nucleic acid sequence encoding a precursor of an insulin analogue according to any of the embodiments 1-35, a derivative thereof, a partial sequence thereof, a degenerated sequence thereof or a sequence which hybridizes thereto under stringent conditions.

Embodiment 49

A vector comprising a nucleic acid according to any of the embodiments 47-48 for expressing of a insulin analogue according to any one of embodiments 1-35.

Embodiment 50

A host cell comprising a vector of embodiment 49 for producing an insulin analogue according to any one of embodiments 1-35.

Embodiment 51

A method for producing an insulin analogue according to any of the embodiments 1-35 by expressing a nucleic acid sequence of embodiments 47-48 encoding the insulin analogue in question in a suitable host cell.

Insulin is a polypeptide hormone secreted by β-cells of the pancreas. Insulin consists of two polypeptide chains, A and B, which are linked by two inter-chain disulphide bridges. Furthermore, the A-chain features one intra-chain disulphide bridge.

The hormone is synthesized as a single-chain precursor proinsulin (preproinsulin) consisting of a prepeptide of 24 amino acids followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

The term "human insulin" as used herein means the human hormone whose structure and properties are well-known. Human insulin has two polypeptide chains that are connected by disulphide bridges between cysteine residues, namely the A-chain and the B-chain. The A-chain is a 21 amino acid peptide and the B-chain is a 30 amino acid peptide, the two chains being connected by three disulphide bridges: one between the cysteines in position 6 and 11 of the A-chain, the second between the cysteine in position 7 of the A-chain and the cysteine in position 7 of the B-chain, and the third between the cysteine in position 20 of the A-chain and the cysteine in position 19 of the B-chain.

By "insulin analogue" as used herein is meant a polypeptide derived from the primary structure of a naturally occurring insulin, for example that of human insulin, by mutation. One or more mutations are made by deleting and/or substituting at least one amino acid residue occurring in the naturally occurring insulin and/or by adding at least one amino acid residue. The added and/or substituted amino acid residues can either be codable amino acid residues or other naturally occurring amino acid residues.

The insulin analogues according to the present invention may be human insulin or an analogue thereof comprising one or more mutations in the A-chain and two or more mutations in the B-chain of the insulin. In one embodiment the insulin analogues are designed for enhanced stability towards proteases based on the identified protease cleavage sites.

In one embodiment an insulin analogue according to the invention comprises less than 8 modifications (substitutions, deletions, additions) relative to the parent insulin. In one embodiment an insulin analogue comprises less than 7 modifications (substitutions, deletions, additions) relative to the parent insulin. In one embodiment an insulin analogue comprises less than 6 modifications (substitutions, deletions, additions) relative to the parent insulin. In another embodiment an insulin analogue comprises less than 5 modifications (substitutions, deletions, additions) relative to the parent insulin. In another embodiment an insulin analogue comprises less than 4 modifications (substitutions, deletions, additions) relative to the parent insulin.

The insulin analogues according to the invention may comprise further mutations. Mutations in the insulin molecule are denoted stating the chain (A or B), the position, and the three letter code for the amino acid substituting the native amino acid. With "desB30" or "B(1-29)" is meant a natural insulin B chain or analogue thereof lacking the B30 amino acid residue and "A(1-21)" means the natural insulin A chain.

Herein terms like A1, A2, A3 etc. indicates the position 1, 2 and 3, respectively, in the A chain of insulin (counted from the N-terminal end). Similarly, terms like B1, B2, B3 etc. indicates the position 1, 2 and 3, respectively, in the B chain of insulin (counted from the N-terminal end). Using the one letter codes for amino acids, terms like A21A, A21G and A21Q designates that the amino acid in the A21 position is A, G and Q, respectively. Using the three letter codes for amino acids, the corresponding expressions are A21Ala, A21Gly and A21Gln, respectively. Thus, A14D, B25H, desB27, desB28, desB29, desB30 human insulin is an analogue of human insulin where position 14 in the A chain is mutated to aspartic acid, position 25 in the B chain is mutated to histidine, and all the positions 27, 28, 29 and 30 in the B chain are deleted.

The term "diabetes" includes type 1 diabetes, type 2 diabetes and other states that cause hyperglycaemia.

The term "treatment" of a disease includes treatment, prevention or alleviation of the disease.

In one embodiment of the invention the insulin analogue is particularly suitable for oral administration.

An "insulin" according to the invention is herein to be understood as human insulin, an insulin analogue or an insulin derivative.

The term "parent insulin" as used herein is intended to mean an insulin before any mutations according to the invention have been applied thereto. Non-limiting examples of parent insulins are e.g. a wild-type insulin such as human insulin or porcine insulin, an analogue of human insulin or a derivative of human insulin or an insulin analogue such as human insulin or an insulin analogue which has been PEGylated or acylated.

In one embodiment a parent insulin according to the invention is human insulin.

A "protease" or a "protease enzyme" is a digestive enzyme which degrades proteins and peptides and which is found in various tissues of the human body such as e.g. the stomach (pepsin), the intestinal lumen (chymotrypsin, trypsin, elastase, carboxypeptidases, etc.) or mucosal surfaces of the GI tract (aminopeptidases, carboxypeptidases, enteropeptidases, dipeptidyl peptidases, endopeptidases, etc.), the liver (Insulin degrading enzyme, cathepsin D etc), and in other tissues.

An insulin analogue according to the invention may be a proteolytically stable insulin analogue.

A proteolytically stable insulin analogue is herein to be understood as an insulin analogue, which is more slowly degraded by one or more proteases relative to human insulin. In one embodiment a proteolytically stable insulin analogue according to the invention is more slowly degraded by one or more proteases relative to the parent insulin. In a further embodiment of the invention an insulin analogue according to the invention is stabilized against degradation by one or more enzymes selected from the group consisting of: pepsin (such as e.g. the isoforms pepsin A, pepsin B, pepsin C and/or pepsin F), chymotrypsin (such as e.g. the isoforms chymotrypsin A, chymotrypsin B and/or chymotrypsin C), trypsin, Insulin-Degrading Enzyme (IDE), elastase (such as e.g. the isoforms pancreatic elastase I and/or II), carboxypeptidase (e.g. the isoforms carboxypeptidase A, carboxypeptidase A2 and/or carboxypeptidase B), aminopeptidase (such as e.g. alanine aminopeptidase or lysine aminopeptidase), cathepsin D and other enzymes present in intestinal extracts derived from rat, pig, dog or human.

In one embodiment an insulin analogue according to the invention is stabilized against degradation by one or more enzymes selected from the group consisting of: chymotrypsin, trypsin, Insulin-Degrading Enzyme (IDE), elastase, carboxypeptidases, aminopeptidases and cathepsin D. In a further embodiment an insulin analogue according to the invention is stabilized against degradation by one or more enzymes selected from the group consisting of: chymotrypsin, carboxypeptidases and IDE. In a yet further embodiment an insulin analogue according to the invention is stabilized against degradation by one or more enzymes selected from: chymotrypsin and carboxypeptidases.

The half-life (T½) of an insulin analogue according to the invention may be determined as described in the Examples as a measure of the proteolytical stability of an insulin analogue according to the invention towards protease enzymes such as chymotrypsin, pepsin and/or carboxypeptidase A. In one embodiment of the invention T½ is increased relative to human insulin. In a further embodiment T½ is increased relative to the parent insulin. In a yet further embodiment T½ is increased at least 2-fold relative to the parent insulin. In a yet further embodiment T½ is increased at least 3-fold relative to the parent insulin. In a yet further embodiment T½ is increased at least 4-fold relative to the parent insulin. In a yet further embodiment T½ is increased at least 5-fold relative to the parent insulin. In a yet further embodiment T½ is increased at least 10-fold relative to the parent insulin.

An insulin analogue according to the invention may have increased potency and/or bioavailability relative to the parent insulin when compared upon measurement.

Standard assays for measuring insulin potency are known to the person skilled in the art and include inter alia (1) insulin radioreceptor assays, in which the relative potency of an insulin is defined as the ratio of insulin to insulin analogue required to displace 50% of $^{125}$I-insulin specifically bound to insulin receptors present on cell membranes, e.g. a rat liver plasma membrane fraction; (2) lipogenesis assays, performed e.g. with rat adipocytes, in which relative insulin potency is defined as the ratio of insulin to insulin analogue required to achieve 50% of the maximum conversion of [3-$^3$H] glucose into organic-extractable material (i.e. lipids); (3) glucose oxidation assays in isolated fat cells in which the relative potency of the insulin analogue is defined as the ratio of insulin to insulin analogue to achieve 50% of the maximum conversion of glucose-1-[$^{14}$C] into [$^{14}$CO$_2$]; (4) insulin radioimmunoassays which can determine the immunogenicity of insulin analogues by measuring the effectiveness by which insulin or an insulin analogue competes with $^{125}$I-insulin in binding to specific anti-insulin antibodies; and (5) other assays which measure the binding of insulin or an insulin analogue to antibodies in animal blood plasma samples, such as ELISA assays possessing specific insulin antibodies. Bioavailability of insulin analogues after per oral administration may e.g. be measured as a ratio of insulin analogue concentration in plasma after per oral administration relative to insulin analogue concentration in plasma after i.v. administration. Alternatively, s.c. administration can be substituted for i.v. administration. Insulin analogue concentration can be determined for example by method (5) listed above.

Insulin analogues according to the invention may optionally be analyzed for further protease sites which may be subject to further substitutions of one or more hydrophobic amino acids with hydrophilic amino acids.

The production of polypeptides, e.g., insulins, is well known in the art. An insulin analogue according to the invention may for instance be produced by classical peptide synthesis, e.g. solid phase peptide synthesis using t-Boc or Fmoc chemistry or other well established techniques, see e.g. Greene and Wuts, "Protective Groups in Organic Synthesis", John Wiley & Sons, 1999. The insulin analogue may also be produced by a method which comprises culturing a host cell containing a DNA sequence encoding the analogue and capable of expressing the insulin analogue in a suitable nutrient medium under conditions permitting the expression of the insulin analogue. For insulin analogues comprising non-natural amino acid residues, the recombinant cell should be modified such that the non-natural amino acids are incorporated into the analogue, for instance by use of tRNA mutants. Hence, briefly, the insulin analogues according to the invention are prepared analogously to the preparation of known insulin analogues.

Several methods may be used for the production of human insulin and human insulin analogues. For example three major methods which are used in the production of insulin in microorganisms are disclosed in WO2008034881. Two of these involve *Escherichia coli*, with either the expression of a large fusion protein in the cytoplasm (Frank et al. (1981) in Peptides: Proceedings of the 7$^{th}$ American Peptide Chemistry Symposium (Rich & Gross, eds.), Pierce Chemical Co., Rockford, Ill. pp 729-739), or use of a signal peptide to enable secretion into the periplasmic space (Chan et al. (1981) PNAS 78:5401-5404). A third method utilizes *Saccharomyces cerevisiae* to secrete an insulin precursor into the medium (Thim et al. (1986) PNAS 83:6766-6770). The prior art discloses a number of insulin precursors which are expressed in either *E. coli* or *Saccharomyces cerevisiae*, vide U.S. Pat. No. 5,962,267, WO 95/16708, EP 0055945, EP 0163529, EP 0347845 and EP 0741188.

The insulin analogues are produced by expressing a DNA sequence encoding the insulin analogue in question in a suitable host cell by well known technique as disclosed in e.g. U.S. Pat. No. 6,500,645. The insulin analogue is either expressed directly or as a precursor molecule which has an N-terminal extension on the B-chain or a C-terminal extension on the B-chain. The N-terminal extension may have the function of increasing the yield of the directly expressed product and may be of up to 15 amino acid residues long. The N-terminal extension is to be cleaved of in vitro after isolation from the culture broth and will therefore have a cleavage site next to B1. N-terminal extensions of the type suitable in the present invention are disclosed in U.S. Pat. No. 5,395,922, and EP 765,395. The C-terminal extension may have the function of protecting the mature insulin or insulin analogue molecule against intracellular proteolytic processing by host cell exoproteases. The C-terminal extension is to be cleaved of either extra-cellularly in the culture broth by secreted, active carboxypeptidase or in vitro after isolation from the culture broth. A method for producing mature insulin and insulin analogs with C-terminal extensions on the B-chain that are removed by carboxypetidase are disclosed in WO 08037735. The target insulin product of the process may either be a two-chain human insulin or a two-chain human insulin analogue which may or may not have a short C-terminal extension of the B-chain. If the target insulin product will have no C-terminal extension of the B-chain, then said C-terminal extension should be capable of subsequently being cleaved off from the B-chain before further purification steps.

The removal of the extension will typically take place by means of a carboxypeptidase activity. The proteolytic step catalysed by such carboxypeptidase activity can take place either by addition of the appropriate enzyme directly to the fermentation broth to process the remaining amino acids residues attached to the C-terminal end of the B-chain in the precursor molecule secreted by the cell.

In addition to the extension of the C-terminal end of the B-chain the insulin molecule may be further modified in the A- and/or B-chain as long as such modification do not have no adverse effect on the insulin activity of the target insulin molecule.

The present invention is also related to nucleic acid sequences which code for the claimed insulin analogues. In a further embodiment the present invention is related to vectors containing such nucleic acid sequences and host cells containing such nucleic acid sequences or vectors.

In still a further embodiment, the invention relates to a process for producing an insulin analogue comprising (i) culturing a host cell comprising a nucleic acid sequence encoding an insulin precursor; (ii) isolating the insulin precursor from the culture medium and (iii) converting the insulin precursor into an insulin analogue of the invention by in vitro enzymatic conversion.

In still a further embodiment, the invention relates to a process for producing an insulin analogue comprising (i) culturing a host cell comprising a nucleic acid sequence encoding an insulin precursor; (ii) isolating the insulin precursor from the culture medium and (iii) converting the insulin precursor into an insulin analogue of the invention.

In one embodiment of the present invention the host cell is a yeast host cell and in a further embodiment the yeast host cell is selected from the genus *Saccharomyces*. In a further embodiment the yeast host cell is selected from the species *Saccharomyces cerevisiae*.

Pharmaceutical Compositions

Another object of the present invention is to provide a pharmaceutical formulation comprising an insulin analogue according to the present invention which is present in a concentration from 0.1 mg/ml to 500 mg/ml, and wherein said formulation has a pH from 2.0 to 10.0. The formulation may further comprise protease inhibitor(s), a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use.

In another embodiment the pharmaceutical formulation is a dried formulation (e.g. freeze-dried or spray-dried) ready for use without any prior dissolution.

In a further embodiment the invention relates to a pharmaceutical formulation comprising an aqueous solution of an insulin analogue of the present invention, and a buffer, wherein said insulin analogue is present in a concentration from 0.1 mg/ml or above, and wherein said formulation has a pH from about 2.0 to about 10.0.

Formulations intended for oral use may be prepared according to any known method, and such formulations may contain one or more agents selected from the group consisting of sweetening agents, flavouring agents, colouring agents, and preserving agents in order to provide pharmaceutically elegant and palatable preparations. Tablets may contain the active ingredient in a mixture with non-toxic pharmaceutically-acceptable excipients which are suitable for the manufacture of tablets. These excipients may be for example, inert diluents, such as mannitol, maltodextrin, kaolin, calcium carbonate, sodium carbonate, lactose, calcium phosphate or sodium phosphate; granulating and disintegrating agents, for example corn starch; binding agents, for example, starch, gelatine, polymers or acacia; and lubricating agents, for example magnesium stearate, stearic acid or talc. The tablets may be uncoated or they may be coated by known techniques to delay disintegration or release of the therapeutically active polypeptide.

The orally administerable formulations of the present invention may be prepared and administered according to methods well known in pharmaceutical chemistry, see Remington's Pharmaceutical Sciences, $17^{th}$ ed. (A. Osol ed., 1985).

In one embodiment of the invention, the pharmaceutical compositions of the present invention may be administered by means of solid dosage forms such as tablets and capsules. The tablets may be prepared by wet granulation, by dry granulation, by direct compression or melt granulation.

Tablets for this invention may be prepared utilizing conventional tabletting techniques. A general method of manufacture involves blending of an insulin analogue, a water-soluble diluent, hydrophilic binder and optionally a portion of a disintegrant. This blend is then granulated with an aqueous solution of the hydrophilic binder or an aqueous solution of the hydrophilic binder and surfactant and milled, if necessary. The granules are dried and reduced to a suitable size. Any other ingredients, such as lubricants, (e.g. magnesium stearate) and additional disintegrants, are added to the granules and mixed. This mixture is then compressed into a suitable size and shape using conventional tabletting machines such as a rotary tablet press. The tablets may be film coated by techniques well known in the art.

Formulations for oral use may also be presented as hard or soft gelatine capsules where the active ingredient is mixed with an inert solid diluent, for example, such as mannitol, maltodextrin, calcium carbonate, sodium carbonate, lactose, kaolin, calcium phosphate or sodium phosphate, or a soft gelatine capsule wherein the active ingredient is mixed with water or an oil medium, for example peanut oil, liquid paraffin, or olive oil.

Capsules for this invention may be prepared utilizing conventional methods. A general method of manufacture involves blending a therapeutically active peptide, alginate, a water-soluble diluent, a hydrophilic binder, and optionally a portion of a disintegrant. This blend is then granulated with an aqueous solution of the hydrophilic binder or an aqueous solution of the hydrophilic binder and surfactant in water, and milled, if necessary. The granules are dried and reduced to a suitable size. Any other ingredients, such as a lubricant, are added to the granules and mixed. The resulting mixture is then filled into a suitable size hard-shell gelatin capsule using conventional capsule-filling machines.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. The preservative is present in an amount sufficient to obtain a preserving effect. The amount of preservative in a pharmaceutical formulation is the well-known to the skilled person and may be determined from e.g. literature in the field and/or the known amount(s) of preservative in e.g. commercial products. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment of the invention the formulation further comprises a chelating agent. The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a stabilizer. The term "stabiliser" as used herein refers to chemicals added to polypeptide containing pharmaceutical formulations in order to stabilize the peptide, i.e. to increase the shelf life and/or in-use time of such formulations. The use of a stabilizer in pharmaceutical compositions is well-known to the skilled person. For convenience reference is made to Remington: *The Science and Practice of Pharmacy*, 19$^{th}$ edition, 1995.

In a further embodiment of the invention the formulation further comprises a surfactant. The term "surfactant" as used herein refers to any molecules or ions that are comprised of a water-soluble (hydrophilic) part, the head, and a fat-soluble (lipophilic) segment. Surfactants accumulate preferably at interfaces, which the hydrophilic part is orientated towards the water (hydrophilic phase) and the lipophilic part towards the oil- or hydrophobic phase (i.e. glass, air, oil etc.). The concentration at which surfactants begin to form micelles is known as the critical micelle concentration or CMC. Furthermore, surfactants lower the surface tension of a liquid. Surfactants are also known as amphipathic compounds. The term "Detergent" is a synonym used for surfactants in general. The use of a surfactant in pharmaceutical compositions is well-known to the skilled person. For convenience reference is made to Remington: *The Science and Practice of Pharmacy*, 19$^{th}$ edition, 1995.

In a further embodiment of the invention the formulation further comprises protease inhibitors.

It is possible that other ingredients may be present in the insulin analogue pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing an insulin analogue according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the insulin analogue compound, increase bioavailability, increase solubility, decrease adverse effects, achieve chronotherapy well known to those skilled in the art, and increase patient compliance or any combination thereof.

Compositions of the current invention are useful in the formulation of solids, semisolids, powder and solutions for pulmonary administration of insulin analogue, using, for example a metered dose inhaler, dry powder inhaler and a nebulizer, all being devices well known to those skilled in the art.

Compositions of the current invention may be useful in the formulation of controlled, sustained, protracting, retarded, and slow release drug delivery systems. More specifically, but not limited to, compositions may be useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles.

Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the insulin analogue compound in the form of a nasal or pulmonal spray. As a still further option, the pharmaceutical compositions containing the insulin analogue compound of the invention can also be adapted to transdermal administration, e.g. by needle-free injection or from a patch, optionally an iontophoretic patch, or transmucosal, e.g. buccal, administration.

The insulin analogue according to the invention can be administered via the pulmonary route in a vehicle, as a solution, suspension or dry powder using any of known types of devices suitable for pulmonary drug delivery. Examples of these comprise of, but are not limited to, the three general types of aerosol-generating for pulmonary drug delivery, and may include jet or ultrasonic nebulizers, metered-dose inhalers, or dry powder inhalers (Cf. Yu J, Chien Y W. Pulmonary drug delivery: Physiologic and mechanistic aspects. Crit Rev Ther Drug Carr Sys 14(4) (1997) 395-453).

In a further embodiment, the formulation could be aerosolized by any known aerosolisation technology, such as nebulisation, to achieve a MMAD of aerosol particles less than 10 μm, more preferably between 1-5 μm, and most preferably between 1-3 μm. The preferred particle size is based on the most effective size for delivery of drug to the deep lung, where protein is optimally absorbed (cf. Edwards D A, Ben-Jebria A, Langer A, Recent advances in pulmonary drug delivery using large, porous inhaled particles. J Appl Physiol 84(2) (1998) 379-385).

Deep lung deposition of the pulmonal formulations comprising the insulin analogue compound may optional be further optimized by using modifications of the inhalation techniques, for example, but not limited to: slow inhalation flow (eg. 30 L/min), breath holding and timing of actuation.

The term “stabilized formulation” refers to a formulation with increased physical stability, increased chemical stability or increased physical and chemical stability.

The term “physical stability” of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the “hydrophobic patch” probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term “chemical stability” of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a “stabilized formulation” refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising the insulin analogue compound is stable for more than 6 weeks of usage and for more than 3 years of storage.

In another embodiment of the invention the pharmaceutical formulation comprising the insulin analogue compound is stable for more than 4 weeks of usage and for more than 3 years of storage.

In a further embodiment of the invention the pharmaceutical formulation comprising the insulin analogue compound is stable for more than 4 weeks of usage and for more than two years of storage.

In an even further embodiment of the invention the pharmaceutical formulation comprising the insulin analogue compound is stable for more than 2 weeks of usage and for more than two years of storage.

Aqueous suspensions may contain the active compounds in admixture with excipients suitable for the manufacture of aqueous suspensions.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These formulations may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical formulations comprising a compound for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, preservative and flavouring and colouring agent.

In a further embodiment of the invention, the formulation further comprises a permeation enhancer. Bile salts and fatty acids are most often considered to increase the oral permeability of the lipid bi-layer membranes of the epithelial cell lining of the GI tract. In general, permeation enhancers increase paracellular and transcellular transport of macromolecules by reversible altering the membrane integrity. The bile salt is selected from the group consisting of cholate, deoxycholate, taurocholate, glycocholate, taurodeoxycholate, ursodeoxycholate, tauroursodeoxycholate, and chenodeoxycholate. The fatty acids is selected from the group of short, medium and long chain fatty acids, such as caprylic acid, capric acid, lauric acid, myristic acid, palmitic acid, stearic acid etc. Others enhancers could be surfactants such as monoglycerides, polyoxyethylene esters, sorbitan surfactants (nonionic) and sulphates (anionic).

In a further embodiment of the invention, the formulation further comprises a mucoadhesive polymer. An intimate contact of the drug delivery system to the mucosa of the gastrointestinal tract can be obtained by use of such a mucoadhesive polymer. An intimate contact of the dosage form to the membrane seems advantageous as an enzymatic degradation of the therapeutically active polypeptide on the way between the delivery system and the absorption membrane can be avoided. Moreover, a step concentration gradient on the absorption membrane representing the driving force for passive drug uptake can be provided.

In a further embodiment of the invention, the formulation further comprises an inhibitor of a proteolytic enzyme(s) to further circumvent the enzymatic barrier and achieving the delivery of the therapeutically active polypeptide such as aminopeptidase inhibitor, amastatin, bestatin, boroleucine and puromycin. Examples of protease inhibitors are sodium glycolate, camostat mesilate, bacitracin, soybean trypsin inhibitor and aprotinin.

Entrapment and encapsulation is a technique used in drug delivery systems for therapeutically active polypeptides to optimize delivery properties including protection against enzymatic degradation. Entrapment or encapsulation could be in the form of polymeric drug delivery systems such as hydrogels and nanocapsules/microspheres, and lipid drug delivery systems such as liposomes and micro emulsions.

Formulations of the current invention may be administered in several dosage forms, for example, as solutions, suspensions, micro- and nano suspension, emulsions, microemulsions, multiple emulsion, foams, salves, pastes, ointments, tablets, coated tablets, effervescent tablets, sublingual tablets, buccal tablets, capsules, for example, hard gelatine capsules and soft gelatine capsules, powder, granules, in situ transforming solutions, for example in situ gelling, in situ setting, in situ precipitating, in situ crystallization, stomach floating formulation such as floating suspension, floating tablet or the like.

In another embodiment, the present invention relates to an insulin analogue according to the invention for use as a medicament.

The term "diabetes" or "diabetes mellitus" includes type 1 diabetes, type 2 diabetes, gestational diabetes (during pregnancy) and other states that cause hyperglycaemia. The term is used for a metabolic disorder in which the pancreas produces insufficient amounts of insulin, or in which the cells of the body fail to respond appropriately to insulin thus preventing cells from absorbing glucose. As a result, glucose builds up in the blood.

Type 1 diabetes, also called insulin-dependent diabetes mellitus (IDDM) and juvenile-onset diabetes, is caused by B-cell destruction, usually leading to absolute insulin deficiency.

Type 2 diabetes, also known as non-insulin-dependent diabetes mellitus (NIDDM) and adult-onset diabetes, is associated with predominant insulin resistance and thus relative insulin deficiency and/or a predominantly insulin secretory defect with insulin resistance.

In one embodiment, an insulin analogue according to the invention is used for the preparation of a medicament for the treatment or prevention of hyperglycemia including stress induced hyperglycemia, type 2 diabetes, impaired glucose tolerance, type 1 diabetes, and burns, operation wounds and other diseases or injuries where an anabolic effect is needed in the treatment, myocardial infarction, stroke, coronary heart disease and other cardiovascular disorders and treatment of critically ill diabetic and non-diabetic patients.

In another embodiment, an insulin analogue according to the invention is used as a medicament for delaying or preventing disease progression in type 2 diabetes.

In one embodiment of the invention, the insulin analogue according to the invention is for use as a medicament for the treatment or prevention of hyperglycemia including stress induced hyperglycemia, type 2 diabetes, impaired glucose tolerance, type 1 diabetes, and burns, operation wounds and other diseases or injuries where an anabolic effect is needed in the treatment, myocardial infarction, stroke, coronary heart disease and other cardiovascular disorders is provided.

In a further embodiment of the invention, a method for the treatment or prevention of hyperglycemia including stress induced hyperglycemia, type 2 diabetes, impaired glucose tolerance, type 1 diabetes, and burns, operation wounds and other diseases or injuries where an anabolic effect is needed in the treatment, myocardial infarction, coronary heart disease and other cardiovascular disorders, stroke, the method comprising administering to a patient in need of such treatment an effective amount for such treatment of an insulin analogue according to the invention, is provided.

The treatment with an insulin analogue according to the present invention may also be combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: GLP-1 and GLP-1 derivatives and analogues, GLP-2 and GLP-2 derivatives and analogues, Exendin-4 and Exendin-4 derivatives and analogues, amylin and amylin derivatives and analogues, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, gastrin and gastrin analogues and derivatives.

It should be understood that any suitable combination of the derivatives according to the invention with one or more of the above-mentioned compounds and optionally one or more further pharmacologically active substances are considered to be within the scope of the present invention.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

Example 1

Proteolytic Stability (Half-Life) of Insulin Analogues and Human Insulin Towards Pepsin Proteolytic stability of human insulin and insulin analogues (0.06 mM, 10 μL) towards pepsin (0.34-3.4 μg) (Pepsin A, Sigma P6887) was measured after incubation in 10 mM HCl, pH 2.0, and 37° C. at a final volume of 100 μL. At various times (0, 5, 15, 30 and 60 min) samples were quenched with an equal volume of 0.1 M TrisHCl, pH 8.0 (final pH 7.7) and transferred to 5° C. Reference samples (0 min) were prepared without adding enzyme. Human insulin and insulin analogues were immediately analyzed by RP-HPLC at 214 nm and the area under the peak corresponding to intact protein was determined. Half-lives ($T_{1/2}$) measured in minutes were obtained from the curves and the fold increase/decrease compared to human insulin (used as internal reference in each experiment) was calculated (Stability relative fold).

Insulin analogues were tested in stability assays and analogues exhibiting enhanced resistance to proteolytic digestion were identified by increased half-lives according to the methods described above. The results demonstrate the potential of the further improved insulin analogues for increased bioavailability due to enhanced resistance to proteolytical degradation and improved solubility. The stability of the following insulin analogues towards pepsin have been tested relative to human insulin.

TABLE 1

| Insulin analogue | $T_{1/2}$ [Min] (Fold) Pepsin |
|---|---|
| A14H, B16H, B25H, desB30 human insulin | 173.3 (258.6) |
| A14E, B16H, B25H, desB27, desB28, desB29, desB30 human insulin | 385.1 (555.6) |
| A14H, B16H, B25H, desB27, desB28, desB29, desB30 human insulin | 239 (344.8) |
| Human insulin | 0.67 (1) |

Example 2

Insulin Receptor Affinity of Selected Insulin Analogues of the Invention

The affinity of insulin analogues of this invention for the human insulin receptor was determined by a SPA assay (Scintillation Proximity Assay) microtiterplate antibody capture assay. SPA-PVT antibody-binding beads, anti-mouse reagent (Amersham Biosciences, Cat No. PRNQ0017) were mixed with 25 ml of binding buffer (100 mM HEPES pH 7.8; 100 mM sodium chloride, 10 mM $MgSO_4$, 0.025% Tween-20). Reagent mix for a single Packard Optiplate (Packard No.

6005190) was composed of 2.4 µl of a 1:5000 diluted purified recombinant human insulin receptor (either with or without exon 11), an amount of a stock solution of A14Tyr[$^{125}$I]-human insulin corresponding to 5000 cpm per 100 µl of reagent mix, 12 µl of a 1:1000 dilution of F12 antibody, 3 ml of SPA-beads and binding buffer to a total of 12 ml. A total of 100 µl reagent mix was then added to each well in the Packard Optiplate and a dilution series of the insulin derivative was made in the Optiplate from appropriate samples. The samples were then incubated for 16 hours while gently shaken. The phases were then separated by centrifugation for 1 min and the plates counted in a Topcounter. The binding data were fitted using the nonlinear regression algorithm in the Graph-Pad Prism 2.01 (GraphPad Software, San Diego, Calif.) and affinities were expressed relative (in percentage (%)) to the affinity of human insulin.

TABLE 2

Insulin receptor affinities of selected insulin analogues of the invention

| Insulin analog | Relative insulin receptor binding affinity (%) |
|---|---|
| A14E, A22K, B16H, B25H, B29R, desB30 human insulin | 7.61 |
| A14E, A22K, B25H, B26G, B27G, B28G, B29R, desB30 human insulin | 59.25 |
| A8H, A14E, A22K, B25H, B29R, desB30 human insulin | 67.09 |
| A8H, A14E, A22K, B25H, B29R, desB30 human insulin | 81.11 |
| A14E, A22K, B16E, B25H, B29R, desB30 human insulin | 0.9 |
| A14E, A22K, B25H, B27E, B29R, desB30 human insulin | 24.6 |
| A14E, B22K, B25H, B26G, B27G, B28G, B29R, desB30 human insulin | 60.67 |
| A14E, B16E, B22K, B25H, B29R, desB30 human insulin | 0.59 |
| A14E, A21G, B25H, desB30 human insulin | 13.12 |
| A14E, B16H, B25H, desB27, desB28, desB29, desB30 human insulin | 1.9 |
| A14H, B16H, B25H, desB27, desB28, desB29, desB30 Human insulin | 2 |
| A14P, B25H, desB30 human insulin | 14 |
| A14E, B27K, desB28, desB29, desB30 human insulin | 79 |
| A14E, A15E, B25H, desB30 human insulin | 23 |
| A14E, B25H, B26E, B27E, desB30 human insulin | 16.5 |
| A14E, B10E, B25H, B26G, B27G, B28G, desB30 human insulin | 144 |
| A8H, A14E, B10E, B25H, B26G, B27G, B28G, desB30 human insulin | 136 |
| A8H, A14E, B16H, B25H, desB30 human insulin | 24 |
| A8H, A14H, B16H, B25H, desB30 human insulin | 27 |
| A14E, B25H, B29R, desB30 human insulin | 26.05 |
| A14E, B16H, B22K, B25H, B29R, desB30 human insulin | 4.61 |
| A14E, B25H, B28G, desB30 human insulin | 18.4 |
| A14E, B25H, B26G, B27G, B28K, desB30 human insulin | 69.54 |
| A14E, B25H, B27G, B28G, desB30 human insulin | 16.48 |
| A14E, B25H, B26G, B27E, B28G, desB30 human insulin | 22.71 |
| A14K, B25H, B29R human insulin | 11 |

Example 3

Degradation of Insulin Analogues Using Duodenum Lumen Enzymes

Degradation of insulin analogs using duodenum lumen enzymes (prepared by filtration of duodenum lumen content) from SPD rats. The assay was performed by a robot in a 96 well plate (2 ml) with 16 wells available for insulin analogs and standards. Insulin analogs ~15 µM were incubated with duodenum enzymes in 100 mM Hepes, pH=7.4 at 37° C., samples were taken after 1, 15, 30, 60, 120 and 240 min. and reaction quenched by addition of TFA. Intact insulin analogs at each point were determined by RP-HPLC. Degradation half time was determined by exponential fitting of the data and normalized to half time determined for the reference insulins or human insulin in each assay. The amount of enzymes added for the degradation was such that the half time for degradation of the reference insulin was between 60 and 180 min. The result was given as the degradation half time for the insulin analog in rat duodenum divided by the degradation half time of the reference insulin from the same experiment (relative degradation rate).

TABLE 3

| Insulin Analog | Duodenum Degradation Relative Stability to human insulin |
|---|---|
| B27K, desB28, desB29, desB30 human insulin | 1.1 |
| A14E, B27K, desB28, desB29, desB30 human insulin | 3.3 |
| A14E, A15E, B25H, desB30 human insulin | 17.6 |
| A14E, B25H, B26E, B27E, desB30 human insulin | 11.55 |
| A14E, B16H, B25H, desB27, desB28, desB29, desB30 human insulin | 0.88 |
| A14H, B16H, B25H, desB27, desB28, desB29, desB30 human insulin | 0.88 |
| A14E, B10E, B25H, B26G, B27G, B28G, desB30 human insulin | 8.14 |
| A8H, A14E, B10E, B25H, B26G, B27G, B28G, desB30 human insulin | 14.85 |
| A8H, A14E, B16H, B25H, desB30 human insulin | 11.55 |
| A8H, A14H, B16H, B25H, desB30 human insulin | 3.3 |
| A14E, B25H, B29R, desB30 human insulin | 9.9 |
| A14E, B16H, B22K, B25H, B29R, desB30 human insulin | 4.4 |
| A14E, A22K, B16H, B25H, B29R, desB30 human insulin | 6.6 |
| A14E, A22K, B25H, B26G, B27G, B28G, B29R, desB30 human insulin | 8.25 |
| A8H, A14E, A22K, B25H, B29R, desB30 human insulin | 7.15 |
| A8H, A14E, B22K, B25H, B29R, desB30 human insulin | 9.9 |
| A14E, B22K, B25H, B26G, B27G, B28G, B29R, desB30 human insulin | 4.4 |
| A14E, A22K, B16E, B25H, B29R, desB30 human insulin | 7.15 |
| A14E, A22K, B25H, B27E, B29R, desB30 human insulin | 20.9 |
| A14E, B16E, B22K, B25H, B29R, desB30 human insulin | 17.05 |
| A14E, A21G, B25H, desB30 human insulin | 6.6 |
| A14P, B25H, desB30 human insulin | 0 |
| A14E, B25H, B28G, desB30 human insulin | 6.05 |
| A14E, B25H, B26G, B27G, B28K, desB30 human insulin | 7.7 |
| A14E, B25H, B27G, B28G, desB30 human insulin | 11 |
| A14E, B25H, B26G, B27E, B28G, desB30 human insulin | 8.25 |
| A14E, B24G, B25H, desB30 human insulin | 2.5 |

The invention claimed is:

1. An insulin analogue selected from the group consisting of:

A14E, A15E, B25H, desB30 human insulin;
A14E, B25H, B26E, B27E, desB30 human insulin;
A8H, A14E, B10E, B25H, B26G, B27G, B28G, desB30 human insulin;
A8H, A14E, B16H, B25H, desB30 human insulin;
A14E, B25H, B29R, desB30 human insulin;
A14E, desB27, desB30 human insulin;
A8H, A14E, B22K, B25H, B29R, desB30 human insulin;
A14E, A22K, B25H, B27E, B29R, desB30 human insulin;
A14E, B16E, B22K, B25H, B29R, desB30 human insulin; and
A14E, A21G, B25H, desB30 human insulin.

2. A pharmaceutical composition comprising the human insulin analogue according to claim 1 and a pharmaceutically acceptable carrier.

3. A method of treating diabetes mellitus in a subject comprising administering to a subject in need thereof a therapeutically effective dose of the pharmaceutical composition according to claim 2.

4. A method of reducing the blood glucose level in a mammal by administering to a mammal in need thereof a therapeutically effective dose of the pharmaceutical composition according to claim 2.

* * * * *